(12) United States Patent
Belley et al.

(10) Patent No.: US 8,747,387 B2
(45) Date of Patent: *Jun. 10, 2014

(54) IV CATHETER WITH IN-LINE VALVE AND METHODS RELATED THERETO

(75) Inventors: Richard A. Belley, St. Louis, MO (US); Richard L. Fiser, Wildwood, MO (US); Eugene E. Weilbacher, Chesterfield, MO (US)

(73) Assignee: Covidien LP, Mansfield, MA (US)

( * ) Notice: Subject to any disclaimer, the term of this patent is extended or adjusted under 35 U.S.C. 154(b) by 992 days.

This patent is subject to a terminal disclaimer.

(21) Appl. No.: 11/974,101

(22) Filed: Oct. 11, 2007

(65) Prior Publication Data

US 2008/0091173 A1    Apr. 17, 2008

Related U.S. Application Data

(63) Continuation-in-part of application No. 11/546,752, filed on Oct. 11, 2006, now Pat. No. 7,695,458.

(60) Provisional application No. 60/840,125, filed on Aug. 25, 2006, provisional application No. 60/726,026, filed on Oct. 11, 2005.

(51) Int. Cl.
    *A61M 25/00*    (2006.01)

(52) U.S. Cl.
    USPC ......................................................... 604/537

(58) Field of Classification Search
    USPC .................... 604/523, 96.01, 164.01–170.03, 604/533–538
    See application file for complete search history.

(56) References Cited

U.S. PATENT DOCUMENTS

| | | | |
|---|---|---|---|
| 4,143,853 A * | 3/1979 | Abramson | 251/149.1 |
| 4,424,833 A | 1/1984 | Spector et al. | |
| 4,874,377 A | 10/1989 | Newgard et al. | |
| 4,895,346 A | 1/1990 | Steigerwald | |
| 4,909,798 A | 3/1990 | Fleischhacker et al. | |
| 4,917,668 A | 4/1990 | Haindl | |
| 4,960,412 A | 10/1990 | Fink | |
| 5,085,645 A | 2/1992 | Purdy et al. | |

(Continued)

FOREIGN PATENT DOCUMENTS

| | | |
|---|---|---|
| WO | WO00/12171 | 3/2000 |
| WO | WO 00/12171 A1 | 3/2000 |
| WO | WO 2007/044878 A2 | 4/2007 |
| WO | WO 2007/079135 A1 | 7/2007 |

OTHER PUBLICATIONS

Corresponding Singapore Application No. 200802635-3 Examination Report, mailed Mar. 31, 2010.
European Search Report EP08836915.2 dated Sep. 28, 2011.

(Continued)

*Primary Examiner* — Aarti B Berdichevsky
*Assistant Examiner* — Bradley Osinski
(74) *Attorney, Agent, or Firm* — Lisa E. Winsor, Esq.

(57) ABSTRACT

A method and apparatus are disclosed for positioning a compression member about the septum of a seal member. In one embodiment, a source of low pressure or vacuum is provided to draw the septum of seal member into the hollow body of the compression member. In an alternative embodiment, a molding apparatus is provided which is dimensioned to receive a compression member and configured to facilitate molding of the septum within the compression member. In another embodiment, the septum of the seal member includes a septum having a tab extending from the septum. The tab is configured to assist positioned of a compression member about the septum.

12 Claims, 35 Drawing Sheets

(56) References Cited

U.S. PATENT DOCUMENTS

| | | |
|---|---|---|
| 5,215,538 A | 6/1993 | Larkin |
| 5,242,393 A | 9/1993 | Brimhall et al. |
| 5,322,518 A | 6/1994 | Schneider et al. |
| 5,335,675 A | 8/1994 | Wheeler et al. |
| 5,390,898 A | 2/1995 | Smedley et al. |
| 5,474,536 A | 12/1995 | Bonaldo |
| 5,487,728 A | 1/1996 | Vaillancourt |
| 5,498,247 A | 3/1996 | Brimhall |
| 5,535,771 A | 7/1996 | Purdy et al. |
| 5,535,785 A | 7/1996 | Werge et al. |
| 5,540,661 A | 7/1996 | Tomisaka et al. |
| 5,555,908 A | 9/1996 | Edwards et al. |
| 5,556,387 A | 9/1996 | Mollenauer |
| 5,562,632 A | 10/1996 | Davila et al. |
| 5,573,516 A | 11/1996 | Tyner |
| 5,676,346 A | 10/1997 | Leinsing |
| 5,738,144 A | 4/1998 | Rogers |
| 5,749,861 A | 5/1998 | Guala et al. |
| 5,776,113 A | 7/1998 | Daugherty et al. |
| 5,788,215 A | 8/1998 | Ryan |
| 5,806,551 A | 9/1998 | Meloul et al. |
| 5,806,831 A | 9/1998 | Paradis |
| 5,817,069 A | 10/1998 | Arnett |
| 5,954,313 A | 9/1999 | Ryan |
| 5,954,698 A | 9/1999 | Pike |
| 5,967,490 A | 10/1999 | Pike |
| 6,068,011 A | 5/2000 | Paradis |
| 6,068,617 A | 5/2000 | Richmond |
| 6,152,900 A | 11/2000 | Mayer |
| 6,158,458 A | 12/2000 | Ryan |
| 6,171,287 B1 | 1/2001 | Lynn et al. |
| 6,228,060 B1 | 5/2001 | Howell |
| 6,482,188 B1 | 11/2002 | Rogers et al. |
| 6,485,473 B1 | 11/2002 | Lynn |
| 6,699,221 B2 | 3/2004 | Vaillancourt |
| 6,740,063 B2 | 5/2004 | Lynn |
| 6,802,490 B2 | 10/2004 | Leinsing et al. |
| 7,691,090 B2 * | 4/2010 | Belley et al. ............ 604/246 |
| 7,695,458 B2 * | 4/2010 | Belley et al. ............ 604/246 |
| 2005/0043684 A1 | 2/2005 | Basta et al. |
| 2007/0083157 A1 * | 4/2007 | Belley et al. ........ 604/93.01 |
| 2007/0100295 A1 * | 5/2007 | Belley et al. ............ 604/246 |

OTHER PUBLICATIONS

JP Office Action 2008-535695 dated Oct. 11, 2011.
JP Office Action 2008-535694 dated Oct. 11, 2011.
Australian First Examiner's Report 2006302049 dated Sep. 13, 2011.
European Office Action corresponding to European Patent Appln. No. 12178986.1 dated Aug. 20, 2013.
European Office Action corresponding to European Patent Appln. No. 12178987.9 dated Aug. 21, 2013.
Japanese Office Action corresponding to Japanese Patent Application No. 2010-529084 dated Aug. 23, 2013.
European Search Report EP12178986 dated Oct. 16, 2012.
European Search Report EP12178987 dated Oct. 17, 2012.
Mexican Office Action dated MX/a/2010/003871 dated Mar. 4, 2013.

* cited by examiner

Section A-A

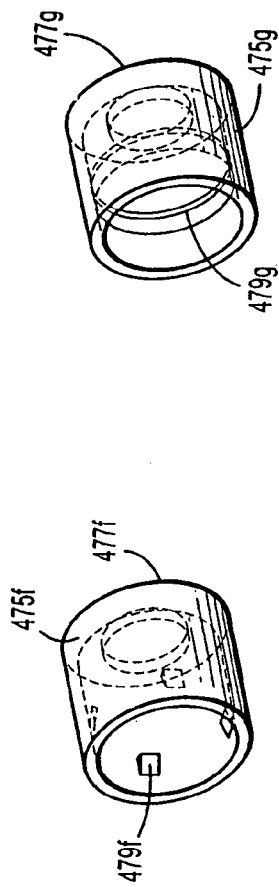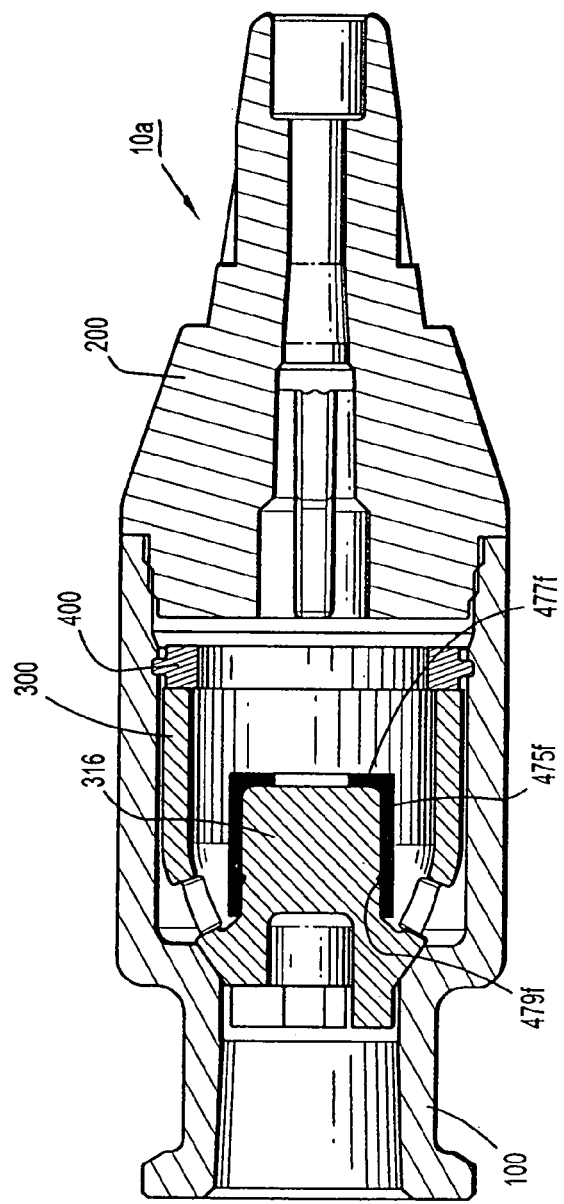

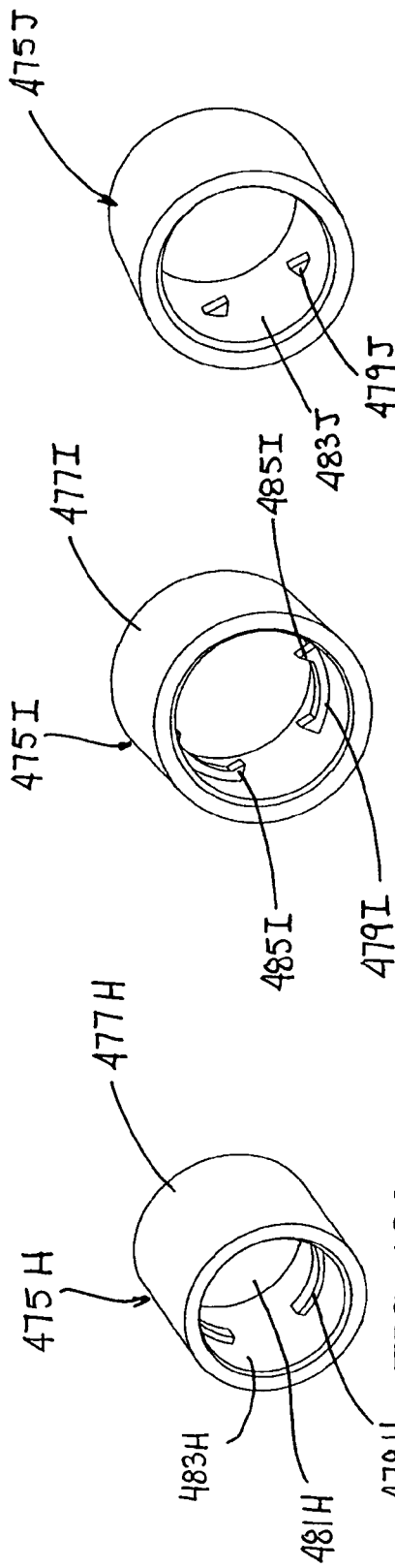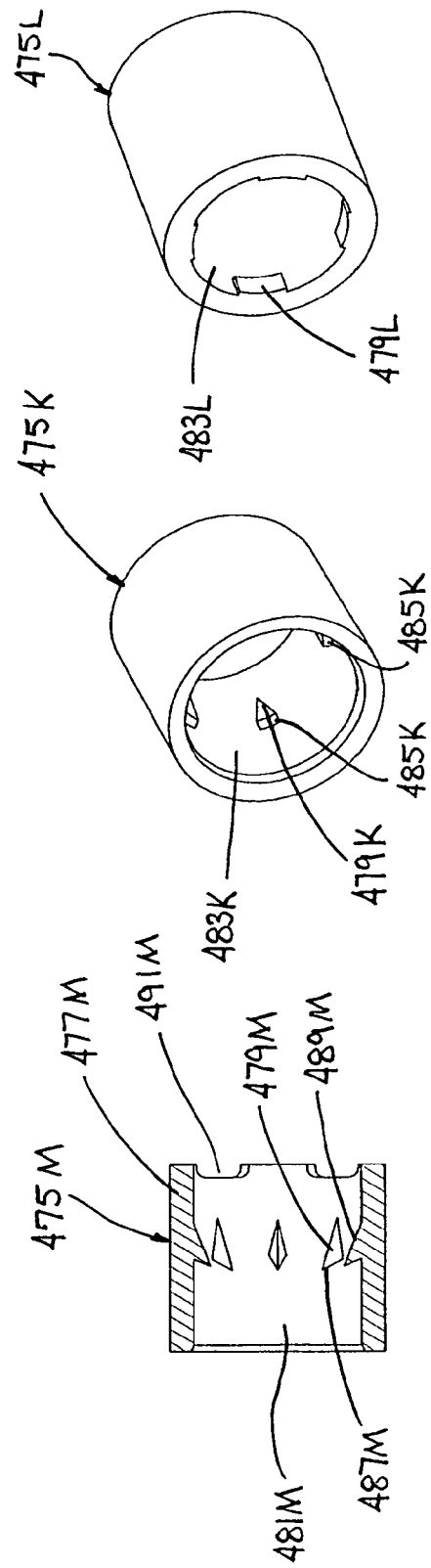

IV CATHETER WITH IN-LINE VALVE AND METHODS RELATED THERETO

This application is a continuation-in-part of U.S. application Ser. No. 11/546,752, filed Oct. 11, 2006, now U.S. Pat. No. 7,695,458 which claims priority from U.S. Provisional Application Ser. No. 60/840,125, which was filed on Aug. 25, 2006, and from U.S. Provisional Application Ser. No. 60/726,026, which was filed on Oct. 11, 2005. The entire contents of each are incorporated herein by reference.

BACKGROUND

1. Technical Field

The present invention generally relates to medical infusion or access devices such as intravenous (IV) catheters and more particularly to a vascular access device including a valve and more specifically to an over-the-needle IV catheter including an in-line valve and having a re-sealable septum compressed by a collar.

2. Description of Related Art

Medical access devices, particularly infusion devices, over-the-needle catheters, other catheters and feeding tubes, are important tools for administration of fluids to patients. In the normal management of a catheter or other medical access device, after it is placed in a patient, it is often necessary to be able to add or withdraw fluids through the device. For example, in surgical procedures, it is a routine practice to place an intravenous catheter so that if it is necessary to medicate a patient during a procedure, the catheter already is in place. It also is common in post surgical situations or in other types of procedures to see medicaments be periodically administered and/or to see fluid sample(s) withdrawn. For example, an IV catheter may be placed in a patient when a stress test is being performed out of caution as well as when the testing process includes injecting a material into the vasculature for use in a subsequent imaging technique.

Over-the-needle catheters or over-the-needle IV catheters (such as that described in PCT Publication No. 2005-0096592) are used for peripheral intravenous entry into the vasculature of a patient. The disposable medical product is packaged as an assembly of a catheter adapter with its catheter and a needle and hub assembly that are arranged with respect to the catheter adapter so the needle passes through the catheter tube. The needle also extends a slight distance beyond the distal tip of the catheter tube so as to provide a sharpened point for penetration through the skin of the human or animal being catheterized.

After the catheter adapter with its catheter and a needle and hub assembly are inserted into the vasculature or blood vessel of the patient, blood flows due to the vascular blood pressure through the hollow needle and into the hub, sometimes referred to as flashback. Typically, the hub is arranged and configured so the medical personnel are provided a visual indicator of the blood flashback thereby indicating the tip of the needle and thus the distal end of the catheter tube is disposed in the blood vessel. One technique used is constructing the hub at least in part of a transparent material so that the blood flashback is visually apparent to the medical personnel.

According to one prior art technique, when flashback is observed, the practitioner or medical personnel places a finger against the skin of the human or animal and presses against the skin so as to compress the skin and the vessel there beneath and thereby occlude vessel blood flow proximal to the catheter tip. Such pressing against the vessel is supposed to thereby prevent the flow of blood back through the catheter tube, into the catheter adapter and out onto the patient, bedding, clothing and the like. Thereafter, the needle and hub as an assembly are removed from the catheter (e.g., the catheter hub is held by the clinician as the needle is being pulled).

While efforts are undertaken in this approach to prevent blood flow back through the catheter tube, such efforts are typically not completely effective and some blood flows onto the patient, bedding, clothing and the like. As such, this approach is of some concern because of the possibility of the spread of communicable diseases, particularly those such as HIV and Hepatitis. As such, a technique has been developed to minimize exposure to blood whereby the needle and hub assembly is removed from the catheter and adapter assembly without having to use the hand which positions the patient's arm to also press and stop blood flow. In this other technique, a mechanism is provided that automatically isolates the blood vessel from the open end of the catheter hub thereby preventing blood loss when the needle and hub assembly is and has been separated from the catheter and adapter assembly.

There is described in U.S. Pat. No. ("USP") 5,085,645 (Purdy et al.), an over-the-needle type of catheter having an adapter including a valve between and in a passage defined in distal and proximal parts of a housing. The described adapter is arranged so as to be an integral part of the catheter hub. In U.S. Pat. No. 5,535,771 (Purdy et al.), there is described a valved adapter for an infusion device.

Others have indicated (see the Background section of U.S. Pat. No. 5,967,490; Pike) that the device described in U.S. Pat. No. 5,085,645 includes an elongate resilient valve (i.e., its length is greater than its width) having a large internal cavity. Such an elongate valve is believed to be unstable and tends to deflect or travel in a non-linear manner during use, thus creating an unreliable seal, possibly resulting in leakage. Valve leakage can create significant discomfort for the patient and increased risk of infection, along with increased risk of exposure to blood borne pathogens for healthcare workers.

Further, the internal cavity of the prior art device has a tendency to collapse during use as a result of the blood pressure of the patient. This could unseat the valve and produce leakage. Also, the internal cavity results in significant "dead" space in the flow path, in which blood or liquid can get trapped. Such trapped fluids can pose a risk of infection and/or thrombosis to the patient. In addition to the above, an elongate valve results in a longer catheter, which is harder for healthcare workers to use while being more expensive to fabricate.

There is described in U.S. Pat. No. 5,967,698 (Pike) a catheter hub including a housing having a connection end defining a first fluid passageway and a catheter end defining a second fluid passageway. The housing includes a plurality of hub walls arranged in a geometric configuration and which hub walls define a valve chamber. The catheter hub further includes a valve positioned in the valve chamber for controlling fluid flow through the chamber between the first and second fluid passageways and an actuator for actuating the valve. The valve is described as being of a substantially cylindrical configuration and is made of a resilient material. In use, a luer projection contacts the actuator, which in turn causes the valve to move axially within the housing thereby opening the valve. The actuator includes an annular flange that is received in a recess in the valve so as to provide structural support to the valve at the actuator end thereof.

There is described in U.S. Pat. No. 5,954,698 (Pike) a catheter apparatus having a needle protector attached to a catheter hub, which needle protector includes a needle. The catheter hub defines a valve chamber, and a valve is positioned in the chamber for controlling fluid flow through the chamber. The valve and catheter hub illustrated therein is the same as that described above for U.S. Pat. No. 5,967,698.

There is described in U.S. Pat. No. 5,817,069 (Arnett) a valve assembly having a body, an end cap, a resilient septum, and an actuator. The body forms a plurality of fluid recesses and the end cap defines a plurality of projections that form channels. The septum is positioned between the body and the end cap. The actuator device is positioned adjacent to the septum so the septum causes the actuator device to be put into sealing engagement with a shoulder defined in the body when in the closed position. When the actuator device is manipulated so the valve assembly is put into the open condition, the actuator device is moved against the septum thereby also moving the actuator device away from the shoulder in the body thereby allowing fluid to pass through the body, actuator, and end cap. The actuator device also is configured with fluid passageways so the fluid flows through the actuator.

There is described in U.S. Pat. No. 5,242,393 (Brimhall et al.) an infusion site for infusing fluids into a patient. The infusion site includes a housing that supports a pre-slit resealable septum, which is held in radial compression in the housing. The housing also accommodates a valve, which is held in tension in the housing and is opened by the insertion of a cannula into the septum. The valve is closed when the cannula is withdrawn. The septum and valve are linked by an elastic member that interacts with the cannula to open and close the valve.

There is described in U.S. Pat. No. 5,788,215 (Ryan) a medical intravenous administration connector including a first coupling member having a female luer, a valve member having a substantially rigid stem and a substantially resilient body with a sealing surface, and a second coupling member having a fluid coupling extending from one end and an internal valve member support. The coupling members are structured to couple to each other with the valve member being biased to a closed position. When assembled, the valve stem extends into the female luer, and the valve body biases the sealing surface against an annular ring in the first coupling member thereby blocking fluid communication. Vanes are provided in the second coupling member on which the resilient body of the valve sits, with the vanes acting as a centering mechanism for the valve. The valve may be opened for fluid flow through the assembly by coupling a male luer to the female luer of the assembly, or by pressure actuation. Several valve members are disclosed and several structures for mating the first and second coupling members are disclosed.

There is described in U.S. Pat. No. 5,215,538 (Larkin) an in-line valve for a medical tubing set that has a tubular member characterized by an internal annular valve seat and a generally circular rubber-like valve member disposed transversely of the tubular member with its edges fixed relative thereto and with a central portion thereof tensioned into seating engagement against the annular valve seat to normally close the in-line valve. Valve member elements are engageable by a connector as same is assembled to the tubular member to move the valve member off of the valve seat to automatically open the in-line valve.

Because there is a large demand for using such IV catheters in surgical and non-surgical environments, it is common to store large number of such IV catheters for ready access for such use or so such IV catheters can be readily shipped to the user. Consequently, the effects of such storage (e.g., cold flow) are a consideration in the design of IV catheters.

There is described in U.S. Pat. No. 6,228,060 (Howell) a blood seal having a spring-biased septum. The spring-biased septum includes an elastic plug with a groove. A biasing element is disposed about the plug within the groove.

There is described in U.S. Pat. No. 5,573,516 (Tyner) a needleless connector having a two-part housing with an inlet, an outlet, and a conical chamber therebetween. The conical chamber compressibly receives a resilient conical valve head. The conical valve head includes a stationary base, and a tip portion movably extending into the inlet. The conical valve head is concentrically positioned against the valve seat to form a seal. When the male fitting of a syringe, or some other device, is inserted into the inlet, it pushes a tip portion of the resilient valve head inwardly, so that the valve head is deformed away from the valve seat to break the seal.

It thus would be desirable to provide a new vascular access device such as an IV catheter device including an in-line valve for controlling the flow of fluid in either direction through the vascular access/IV catheter device and methods related thereto. It would be particularly desirable to provide such a device in which the seal member of the valve is sealingly disposed and retained only within a proximal portion of the device. It would be further desirable to provide a valve member suited for long-term storage with the needle or cannula inserted therethrough. It also would be desirable to provide such a device that is less complex in structure, manufacture and operation as compared to prior art devices. Also it would be desirable that such methods would not require highly skilled users to utilize the catheter device.

SUMMARY

A method for positioning a compression member about a septum of a seal member is described which includes, the steps of 1) providing a compression member having a hollow body with a first open end and a second open end; 2) providing a seal member having a septum and a tab extending from the septum; 3) positioning the compression member about the tab adjacent the septum; and 4) moving the tab relative to the compression member about the septum of the seal member. In one embodiment, the septum and the tab are longitudinally aligned. The tab can be substantially cylindrical. Alternatively, other configurations are envisioned.

In one embodiment, the method further includes the step of removing the tab from the septum after the compression member is positioned about the septum. The step of removing can include cutting the tab from the septum.

A method for positioning a compression member about a septum of a seal member is also described which includes the steps of 1) providing a compression member having a hollow body with a first open end and a second open end; 2) providing a septum having a body formed of an elastomeric material; 3) providing an apparatus including a source of low pressure and a conduit having a first end and a second end, the second end of the conduit communicating with the source of low pressure; 4) supporting the compression member on the first end of the conduit; 5) operating the apparatus to provide a reduced pressure within the conduit and within the compression member; and 6) drawing the septum into the compression member using the reduced pressure within the compression member. In one embodiment, the apparatus further includes a pressurized chamber and the drawing step is conducted within the pressurized chamber. The septum can be preslit to facilitate insertion and removal of a medical device. In one embodiment, the septum forms a portion of a seal member.

A method for positioning a compression member about a septum of a seal member is also disclosed which includes the steps of 1) providing a compression member having a hollow body with a first open end and a second open end; 2) molding a bell portion of a seal member to the compression member; and 3) inserting a septum of the seal member into one of the first and second open ends of the compression member. A method of positioning a compression member about a septum of a seal member is also disclosed which includes the steps of 1) providing a compression member having a body including circular upper and lower body portions which are interconnected by converging end portions to define a substantially eye-shape; 2) positioning the compression member about a septum of a seal member; and 3) crimping the end portions of the compression member about the septum to secure the compression member about the septum. In one embodiment, the septum of the seal member includes a slit for receiving a medical device. Further, the compression member can be dimensioned to provide compression on the septum to assist in resealing the slit after a medical device has been removed from the septum.

An IV catheter device is also disclosed which includes a housing defining a chamber. A seal member is positioned within the chamber and includes a sealing portion which is positioned to engage a seating surface within the housing to seal a proximal portion of the chamber from a distal portion of the chamber. A locking member is positioned within the chamber of the housing. The locking member is positioned about and engages the seal member to position the sealing portion of the seal member in engagement with the seating surface. The locking member includes at least one channel connecting a proximal portion of the chamber to a distal portion of the chamber. When the sealing portion of the seal member is moved from engagement with the seating surface within the housing, fluid can flow about the sealing member and through the at least one channel to the distal portion of the chamber. In one embodiment, the locking member has a substantially annular body.

An external periphery of the locking member can be secured to an inner wall of the housing and an internal periphery of the locking member can be secured to the seal member. In one embodiment, the inner periphery of the locking member includes an annular rim configured to receive a distal end of the seal member. The at least one channel may include a plurality of channels positioned about the annular body of the locking member. The IV catheter device may also include a tubular member defining a lumen in fluid communication with the distal portion of the chamber.

An IV catheter device is also disclosed which includes a housing defining a chamber, a tubular member extending distally from the housing and defining a lumen, the lumen being in fluid communication with the chamber, and a seal member disposed within the chamber. The seal member has a sealing portion and a septum configured to removably receive an introducer needle. The sealing portion of the seal member is movable into sealing engagement with a portion of the housing. The IV catheter device also includes a compression member coupled to the seal member about the septum. The compression member has a substantially cylindrical shape and has an internal surface including at least one friction element. Each at least one friction element includes an angled, distally extending barb having an apex and a sloped proximal surface. The sloped proximal surface of the barb being configured to facilitate placement of the compression member about the septum. The apex being configured to provide a retention force to retain the compression member about the septum.

In one embodiment, the compression member includes indicia configured to provide an indication that the compression member has been properly positioned on the septum. The indicia may include one or more cutouts formed on the distal end of the compression member.

The indicia may also include one or more tabs formed on a distal end of the compression member. The one or more tabs may be configured to provide an indication that the compression member has been properly positioned on the septum when the distal end of the tabs are positioned flush with a distal face of the septum. The one or more cutouts can include a plurality of cutouts and the one or more tabs can include a plurality of tabs.

DEFINITIONS

The instant/present invention is most clearly understood with reference to the following definitions:

The term "co-planar septum" shall be understood to mean a septum that is located essentially on the same axial plane as the seat area.

The term "proximal" shall be understood to mean or refer to a location on the device object or part being discussed which is closest to the medical personnel and farthest from the patient in connection with whom the device is used when the device is used in its normal operation.

The term "distal" shall be understood to mean or refer to a location on the device, object or part being discussed which is farthest from the medical personnel and closest to the patient in connection with whom the device is used when the device is used in its normal operation.

The term "medical personnel" shall be understood to be generally inclusive of clinicians, surgeons, medical technicians, lab technicians, nurses and the like.

The term "patient" shall be understood to include both human and animals and also shall be inclusive of humans or animals that are undergoing medical procedures including but not limited to surgical procedures and diagnostic procedures, medical treatments and/or other techniques/procedures/treatments performed in hospitals, clinics, doctor's offices, diagnostic facilities/laboratories or the like.

BRIEF DESCRIPTION OF THE DRAWINGS

For a fuller understanding of the nature and desired objects of the present invention, reference is made to the following detailed description taken in conjunction with the accompanying drawing figures wherein like reference characters denote corresponding parts throughout the several views whenever possible and wherein:

FIG. 9A is a perspective view of another compression member for use in an IV catheter;

FIG. 9B is an assembled, cross-sectional, perspective view of an IV catheter with the compression member of FIG. 9A in place;

FIG. 10 is a perspective view of yet another compression member for use in an IV catheter;

FIG. 10A is a perspective view of another compression member for use with an IV catheter;

FIG. 10B is a perspective view of another compression member for use with an IV catheter;

FIG. 10C is a perspective view of another compression member for use with an IV catheter;

FIG. 10D is a perspective view of another compression member for use with an IV catheter;

FIG. 10E is a perspective view of another compression member for use with an IV catheter;

FIG. 10G is a cross-sectional view of the compression member shown in FIG. 10F;

DESCRIPTION OF EMBODIMENTS

Figure 1:
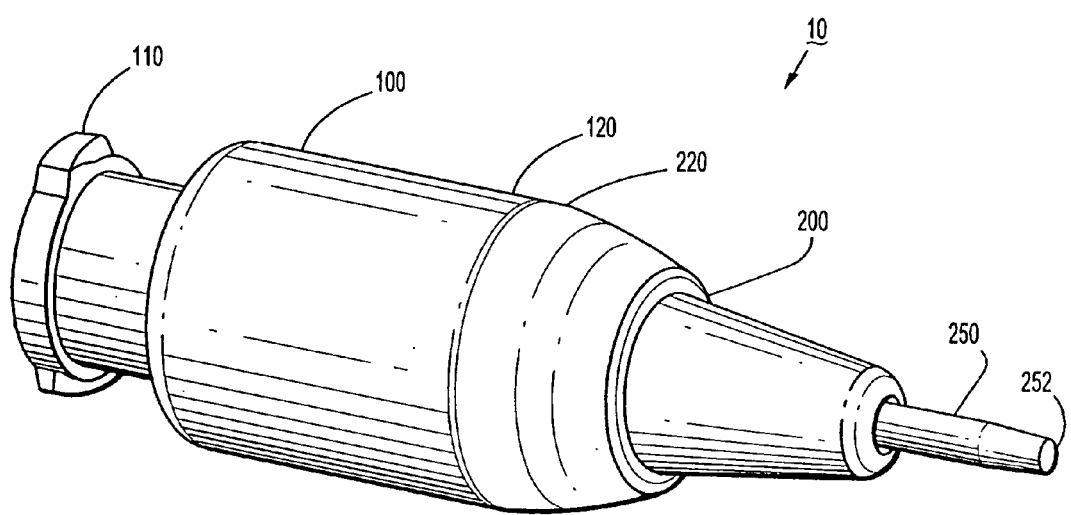
FIG. 1 is an axonometric view of an in-line valve IV catheter.

Referring now to the various figures of the drawings wherein like reference characters refer to like parts, there is shown in FIG. 1 an axonometric view of an in-line valve IV catheter assembly 10, which is a type of vascular access device, that is of the catheter-over-stylet/sharp/cannula type of IV catheter (Note: The catheter length is represented shorter than usual for simplicity). The stylet/sharp/cannula 20 (e.g., see FIGS. 2A,I) is inserted through the IV catheter assembly 10 or IV catheter so that the piercing end of the stylet/sharp/cannula 20 extends out of the open end 252 of the catheter tubular member 250. In this way, and as known to those skilled in the art, a user inserts the piercing end of the stylet/sharp/cannula 20 through the skin and subcutaneous tissue of the body so that the open end 252 of the tubular member 250 of the IV catheter assembly 10 is disposed within the blood vessel (e.g., vein or artery) of the patient.

Referring now to FIG. 1, the in-line valve IV catheter assembly 10 includes a proximal housing 100 with a mating end 120 and a distal housing 200 with a mating end 220 that are secured to each other so as to form an integral unit and so as to form a pressure boundary. Although not shown in FIG. 1 (e.g., see FIG. 2A) such an in-line valve IV catheter assembly 10 also includes a seal member 300 and a locking ring member 400 that sealingly secures the seal member within the proximal housing (i.e., in the sealing configuration). When in the valve closed configuration, at least a portion of the seal member 300 sealingly engages some inner surfaces of the proximal housing 100 thereby preventing fluid flowing in either proximal or distal directions through the in-line valve IV catheter assembly 10. When fluid flow in either direction through the in-line valve IV catheter 10 is desired (i.e., the valve open configuration), the seal member 300 is manipulated so at least a portion of the seal member in sealing engagement with inner surfaces of the proximal housing 100 is displaced from these inner surfaces. As is more particularly described herein, such displacement establishes an open fluid flow path within the proximal housing in either the proximal or distal directions.

A coupling end 110 of the proximal housing 100 is generally configured so as to be removably coupled to an external device (not shown) such as syringe, IV drip, IV pump or the like so as to allow a fluid sample(s) to be removed from the patient via the IV catheter assembly 10 or so fluid can be injected into the patient via the IV catheter assembly. In particular illustrative embodiments, the proximal housing coupling end 110 is configured to form a luer lock type end connection as is known to those skilled in the art, although the end connection can be any of a number of connections known or hereinafter developed that is appropriate for the intended use. It also should be recognized that such fluid being injected also can contain or be adapted or be adjusted so as to include any of a number of medicaments, drugs, antibiotics, pain medication and the like as is known to those skilled in the art for treatment and/or diagnosis.

Now referring to FIGS. 2A-I, there are shown various views of an in-line valve IV catheter assembly 10a according to one aspect and components or features thereof. Such an in-line valve IV catheter assembly 10a includes a proximal housing 100, a distal housing 200, a seal member 300, a locking ring member 400 and a compression member or collar 475. Throughout the present disclosure, the structure identified by reference character 475 may be interchangeably referred to as either "the compression member" or "the collar." Reference shall be made to the foregoing discussion of the proximal and distal housings 100, 200 of FIG. 1 for further details of the proximal and distal housings 100, 200 not otherwise described below.

Figure 2A:
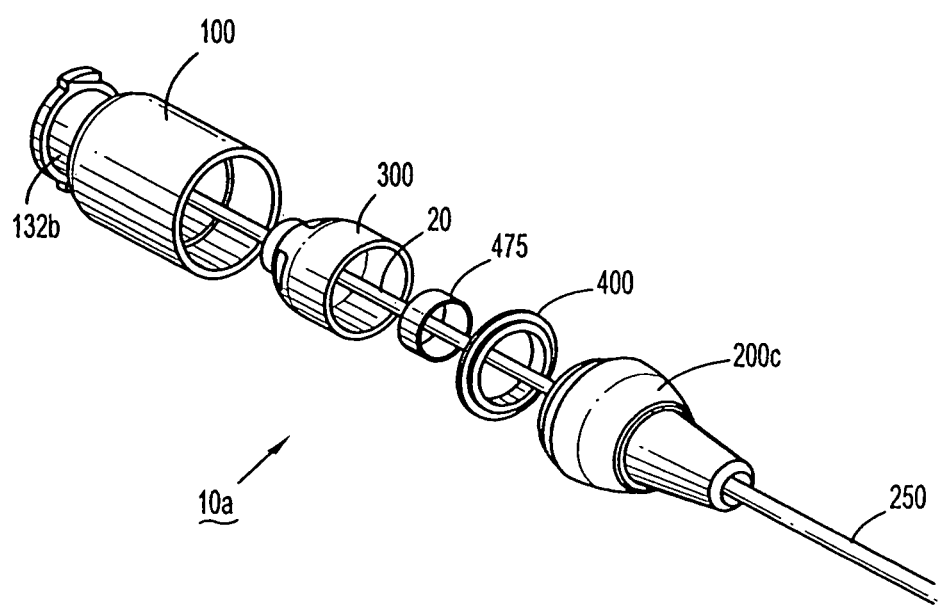
FIG. 2A is an exploded view of another aspect of an in-line valve IV catheter having a seal member with a septum having a compression collar.
Figure 2B:
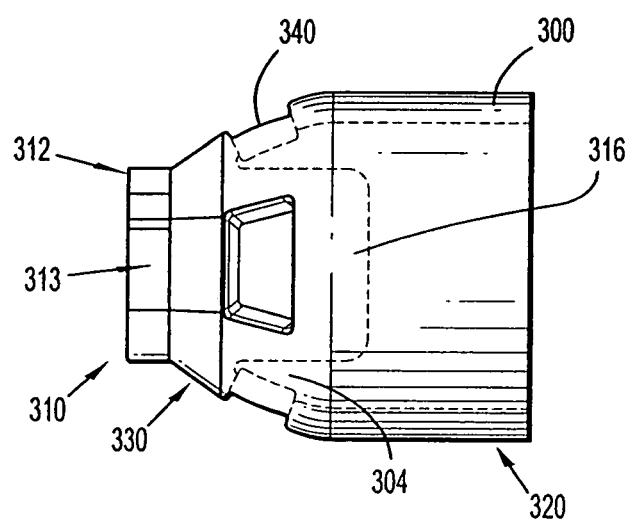
FIG. 2B is a side view of a seal member with a remote septum for use in the IV catheter of FIG. 2A.
Figure 2C:
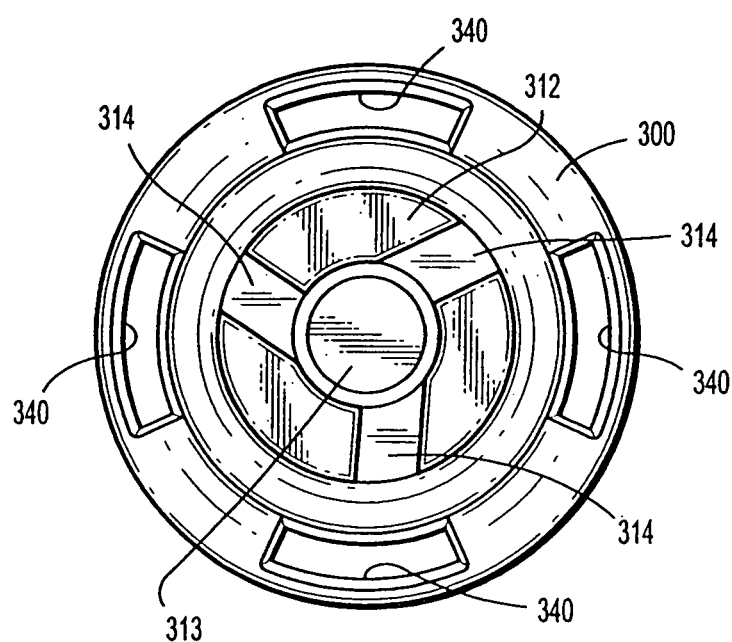
FIG. 2C is a proximal end view of a seal member with a remote septum for use in the IV catheter of FIG. 2A.
Figure 2D:
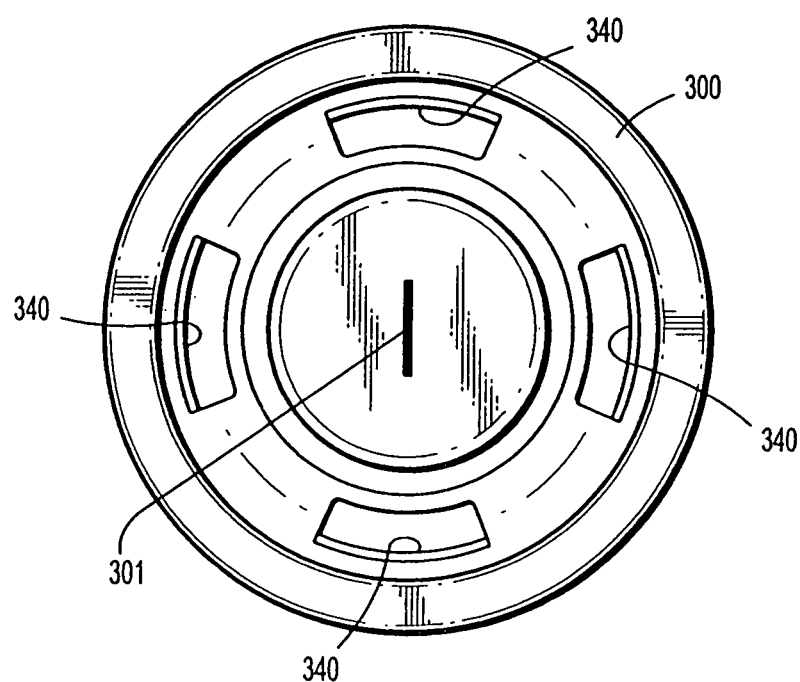
FIG. 2D is a distal end view of a seal member with a remote septum for use in the IV catheter of FIG. 2A.
Figure 2E:
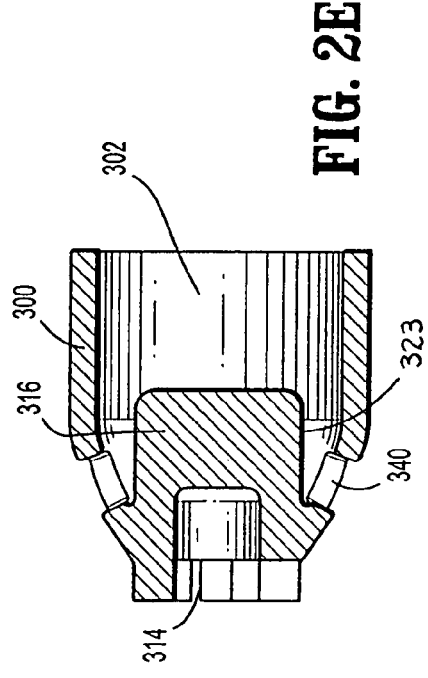
FIG. 2E is a cross-sectional view of a seal member with a remote septum for use in the IV catheter of FIG. 2A.
Figure 2H:
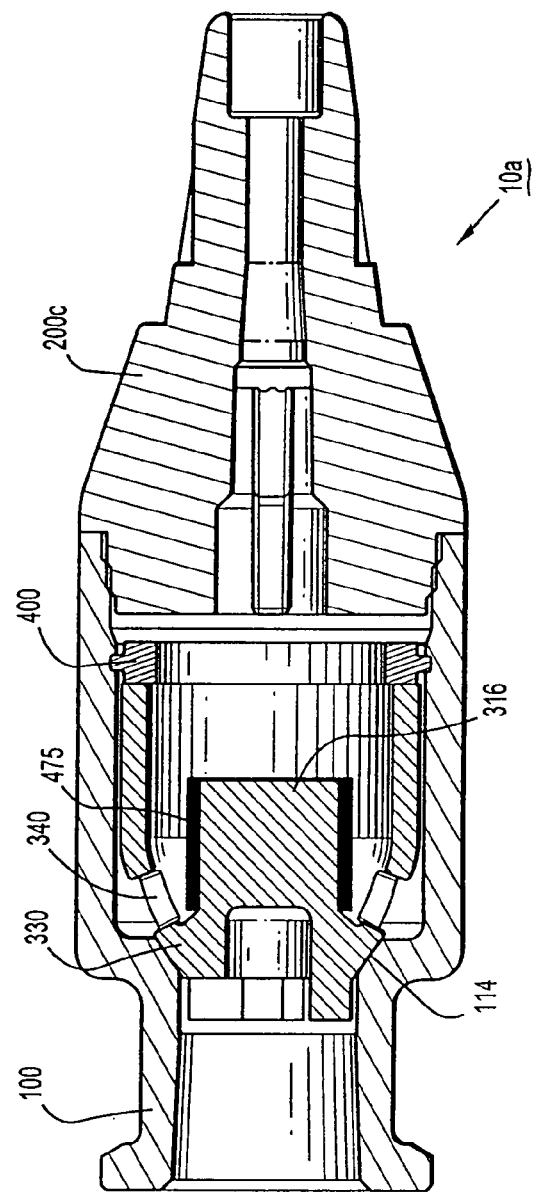
FIG. 2H is an assembled, cross-sectional, perspective view of the IV catheter of FIG. 2A without the stylet in place.
Figure 2F:
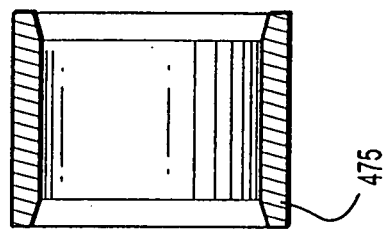
FIG. 2F is a side view of a compression collar for use in the IV catheter of FIG. 2A.
Figure 2G:
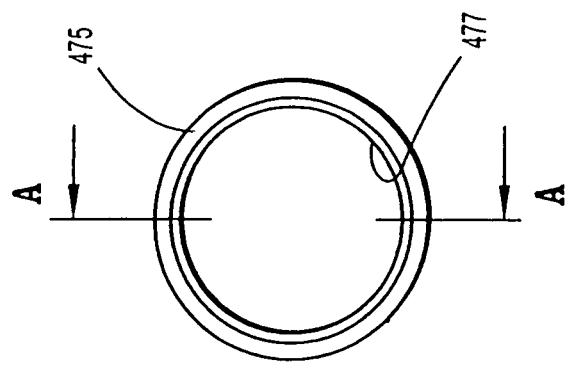
FIG. 2G is an end view of a compression collar for use in the IV catheter of FIG. 2A.

As more particularly illustrated in FIGS. 2H,I, the proximal and distal housings 100, 200 are joined to each other to form a pressure boundary body of the IV catheter assembly 10a. It is noted that no part of the distal housing 200 acts on or applies a force to the seal member 300 so as to thereby cause the seal member to be put into sealing engagement with some inner surfaces of the proximal housing 100. Rather, the sealing engagement results from the compression of the seal member 300 by the locking ring member 400 when the ring member is secured to the proximal housing 100 at a predetermined location within the proximal housing 100.

In exemplary, illustrative embodiments, the seal member 300 is a bell shaped member (e.g., see FIG. 2B). Other shapes, however, can be utilized and thus are contemplated which other shapes are generally characterized as being capable of exhibiting or achieving the herein described mechanical and sealing characteristics for the seal member 300. The seal member 300 also is constructed of a generally resilient material (e.g., an elastomeric material) that allows at least a portion of the seal member to be compressed and/or axially moved along its long or longitudinal axis as herein further described. It should be recognized the foregoing shall not be construed as being limiting as it is contemplated that the seal member can be constituted of materials having different characteristics including different structural or flexibility characteristics.

Such a seal member 300 includes a proximal end 310, a distal portion 320, a sealing portion 330, an inner cavity 302 (FIG. 2E) and one or more of windows 340 or through-apertures. In more particular embodiments, the seal member 300 includes a plurality of such windows 340. As described herein in more detail, such compression or axial movement occurs when an axial force is applied to the proximal end 310 of the seal member 300 such as for example a portion of the coupling device being removably coupled to the coupling end 110 of the proximal housing 100.

Each window 340 in the seal member 300 is arranged so it extends between an exterior surface 304 of the seal member 300 and the inner seal member cavity 302 thereof whereby fluid can flow in one direction through each of the windows into the inner cavity (such as when fluid is being injected into the patient) or can flow in the opposite or another direction through the inner cavity and out through the one or more windows 340 (such as when fluid is being extracted from the patient such as for sampling purposes). The number, shape and size of windows 340 is set so that the resultant cross-sectional area is appropriate to establish the desired fluid flow conditions (e.g., desired pressure loss and flow volume).

The proximal end 310 of the seal member 300 includes one or more raised sections 312 (FIGS. 2B and 2C) arranged about a centrally positioned chamber 313 and one or more passages or channels 314 between each of the one or more raised sections and which are fluidly coupled with the central chamber. The proximal end 310 also includes a septum 316. The raised sections 312 and the channels cooperate so that when the sealing portion 330 of the seal member 300 is displaced from the proximal housing seating surface 114 (FIG. 2H), one or more flow paths (FIG. 15C) are established between the centrally positioned chamber 313. Thus, when the sealing portion 330 is displaced from the seating surface 114 of the proximal housing 100 corresponding to a valve open condition, fluid can flow from/to the coupling end 110 of the proximal housing, through the centrally positioned chamber 313 and the channels 314; about the seal member 330 and through the seal member windows 340, through the seal member inner cavity 302, through a portion of the distal housing inner cavity 230 (e.g., see FIG. 2I) and to/from the open end 252 of the tubular member 250.

Figure 2I:
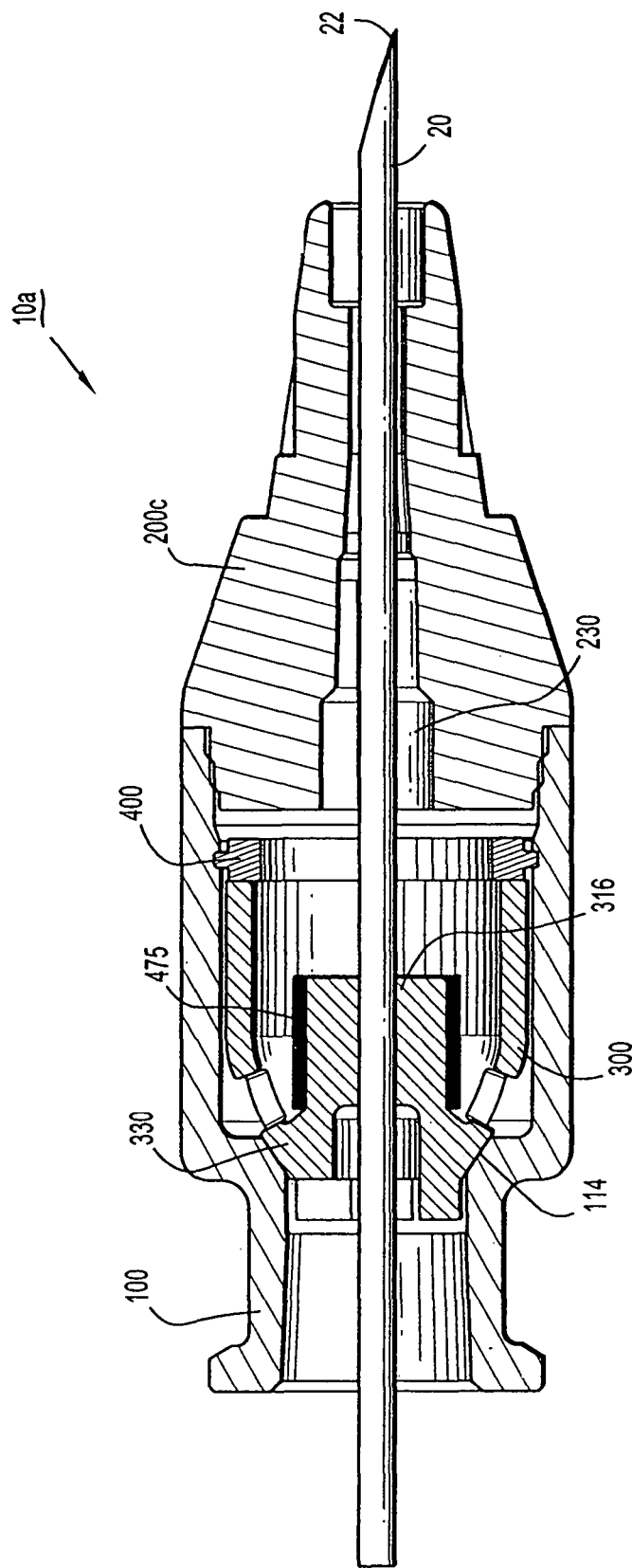
FIG. 2I is an assembled, cross-sectional, plan view of the aspect of the IV catheter of FIG. 2A with the stylet in place and the tubular member omitted for simplicity.
Figure 15A:
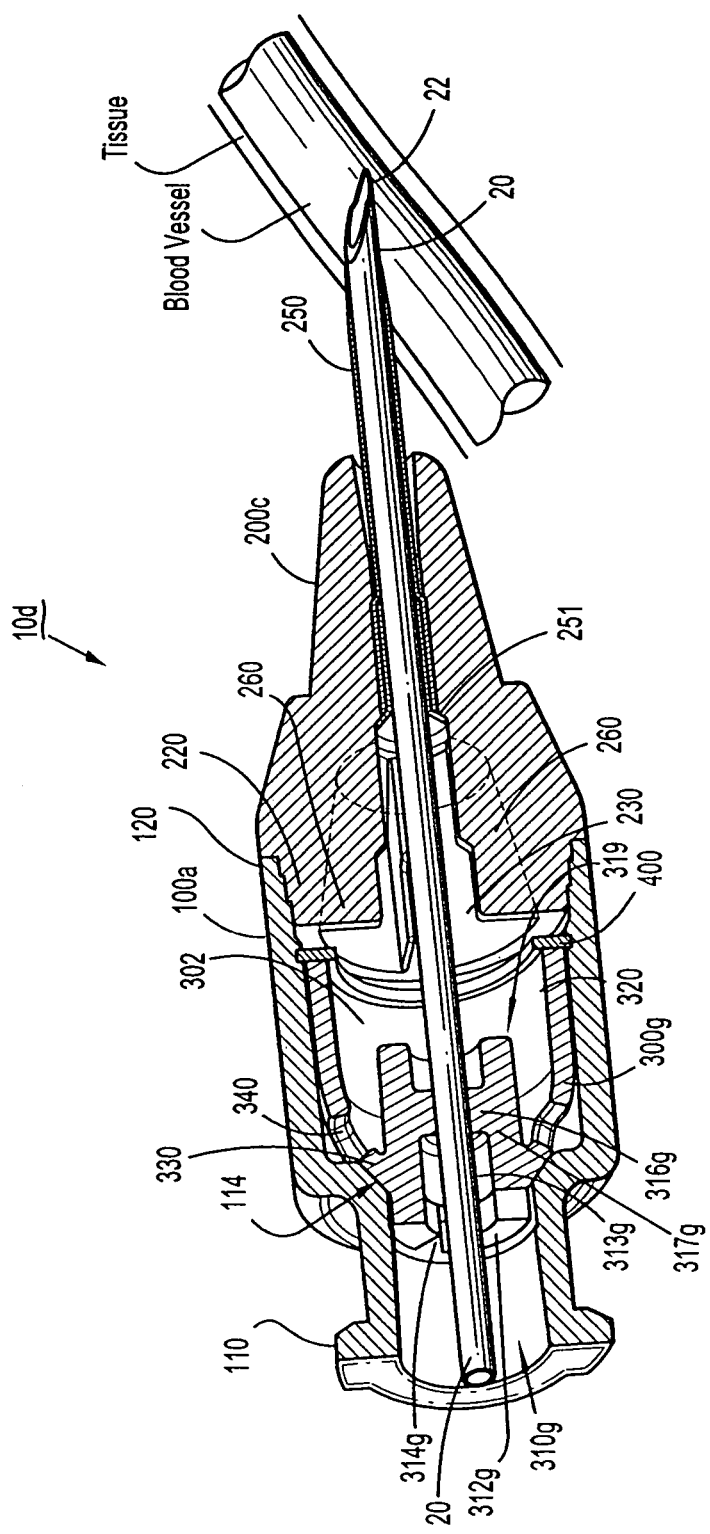
FIGS. 15A, B are cross-sectional views of the in-line valve IV catheter illustrating an exemplary use of such an IV catheter.

Prior to use as an IV catheter, and as illustrated in FIGS. 2I and 15A, a stylet/sharp/cannula 20 is disposed to pass through the centrally positioned chamber 313, through the septum 316 and through the seal member inner cavity 302. As also shown in FIG. 2A, the stylet/sharp/cannula 20 also passes through the second portion 132b of the proximal housing 100, the centrally located opening or through aperture in the locking ring member 400, through the inner cavity 230 of the distal housing 200 and out through the tubular member 250. The septum 316 and the proximal end 310 of seal 300 are made of a resilient material(s) that will re-seal themselves after the stylet/sharp/cannula 20 is withdrawn through the septum. It is contemplated that the sharp end of the stylet/sharp/cannula 20 can be used to form the opening in the septum through which it would pass or another device or instrumentality can be used to form the opening initially in the septum 316 and thereafter the stylet/sharp/cannula 20 would be inserted through this initially formed opening by the opposite end or the sharp end of the cannula.

As shown in more clearly in FIG. 2I, the proximal end 310 of the seal member 300 extends into the second portion 132b of the inner cavity 130 of the proximal housing 100 when the sealing portion 330 of the seal member 300 is in sealing engagement with the seating surface 114 which corresponds to the valve closed condition. In use, when a portion of a syringe or other device 2 (FIGS. 15B,C) is inserted into the opening in the coupling end 110 of the proximal housing 100, the syringe or other device portion contacts and pushes against the proximal end 310 of the seal member 300, more specifically contacts and pushes against the raised sections 312 of the proximal end. Such contacting or pushing thereby causes a force (e.g., an axial force) to be applied to the seal member proximal end 310 to thereby axially displace or move the sealing portion from the seating surface 114 as illustrated for example in FIG. 15C. As also indicated herein, such syringe or other device would be secured (i.e., removably secured) to the coupling end 110 of the proximal housing 100 using any of a number of techniques known to those skilled in the art (e.g., a luer connection).

As indicated above, such displacing opens up the valve embodied in the in-line valve IV catheter assembly 10 and also creates a flow path through the in-line valve IV catheter assembly. When the valve is thus opened, a fluid pathway is thereby established between the syringe or other device and the open end 252 of the tubular member 250. In this way, fluid can flow in either direction through the in-line valve IV catheter assembly as described in more detail herein so that fluid can be introduced into the blood vessel in which the tubular member 250 is inserted into or so a fluid sample can be extracted from such a blood vessel.

When the syringe or other device is decoupled from the coupling end 110 and removed from the second portion 132b (FIG. 2A), the force that was acting on the proximal end 310 of the seal member 300 is removed. When such force is removed, the resiliency of the seal member 300 causes the seal member to move axially towards the seating surface 114 (i.e., away from the locking ring member 400) until the sealing portion 330 thereof sealingly engages the seating surface 114 (FIG. 2H) of the proximal housing 100. In this way, the valve formed by the cooperation of the proximal housing 100, the seal member 300 and the locking ring member 400 is again closed preventing flow of fluid through the in-line valve IV catheter assembly 10a. The foregoing described operation of coupling a syringe or other device to the proximal housing 100 can be repeated as and when needed/desired by medical personnel.

Referring now to FIGS. 2A-I, there are several views of another aspect of an in-line valve IV catheter 10a and various parts such as a seal member 300 with a septum 316 and a compression member 475. The compression member 475 is disposed about the septum 316 so that a radially compressive force is applied to the septum 316. A beneficial effect of enhancing the ability of the septum 316 to reseal is to minimize the potential for leakage through the septum 316 after removal of the stylet/sharp/cannula 20. Such an in-line valve IV catheter 10a also is shown with an insertion stylet/sharp/cannula 20 that is inserted therethrough (e.g., see FIG. 2I).

In one embodiment, the septum 316 has a preformed slit or passage 301 for the stylet/sharp/cannula 20 and the compression member 475 has an inner diameter 477 (FIG. 2G) smaller than the outer diameter 323 (e.g., see FIG. 2E) of the septum 316 to provide adequate restorative force. A plurality of factors govern the ideal sizing relationship between the inner diameter 477 of the compression member 475 and outer diameter 323 of the septum 316 such as the material of the septum 316, the manufacturing tolerances of the septum 316 and compression member 475, the diameter of the stylet/sharp/cannula 20, the ease of assembly and like factors as would be appreciated by those of ordinary skill in the pertinent art. Before insertion of the stylet/sharp/cannula 20, the ratio of inner diameter 477 of the compression member 475 to the outer diameter 323 of the septum 316 could be approximately 1.0 and insertion of the stylet/sharp/cannula 20 would create compression. In one embodiment, the ratio (cannula not in place) is in the range of approximately 0.79 to 0.92, and can be between about 0.82 to about 0.88.

In a further embodiment, the axial width of the collar 475 is longer than the axial width of the septum 316 such that the entire septum 316 is uniformly compressed, as the septum expands axially due to the radial compression. The compression member 475 may be composed of a rigid bio-compatible material such as stainless steel, plastic (e.g. polycarbonate) or like material to lend circumferential rigidity and strength to the septum.

During assembly, the septum 316 is fit within the compression member 475 and the stylet/sharp/cannula 20 passes through the septum 316 in a ready-to-insert position. In further embodiments, the compression member 475 is formed of an elastic or semi-resilient material having different elastomeric characteristics (e.g., thickness, resiliency) than the seal member so that the septum is similarly maintained in a radial compression.

Without being bound to any particular theory or principle of science, the compression member 475 enhances the ability of the septum 316 to self-close or self-seal itself after the insertion stylet/sharp/cannula 20 is removed from the septum 316. Also, the compression member 475 enhances the ability of the septum 316 to limit or resist propagation of any tears that may originate in the septum 316. These advantageous effects are attributed to the presence of the compression member 475 and the effect such a structure has on enhancing or increasing the radial stiffness of the septum 316.

In the event that the storage extends for a number of years, the radial compression provided by the compression member 475 in tandem with the resiliency and sealing properties of the septum 316 establishes an effective sealing force after removal of the stylet/sharp/cannula 20 so as to thereby cause the opening 301 in the septum 316 for the stylet/sharp/cannula 20 to reseal itself. It is also envisioned that the compression member 475 can be effectively used with this embodiment and other similar embodiments shown herein and elsewhere. Additionally, technology is also disclosed herewith to prevent the potential for blood leakage following removal of the insertion stylet/sharp/cannula 20. Such technology may be used solely or in conjunction with the other devices and structures herein.

Figure 3A:
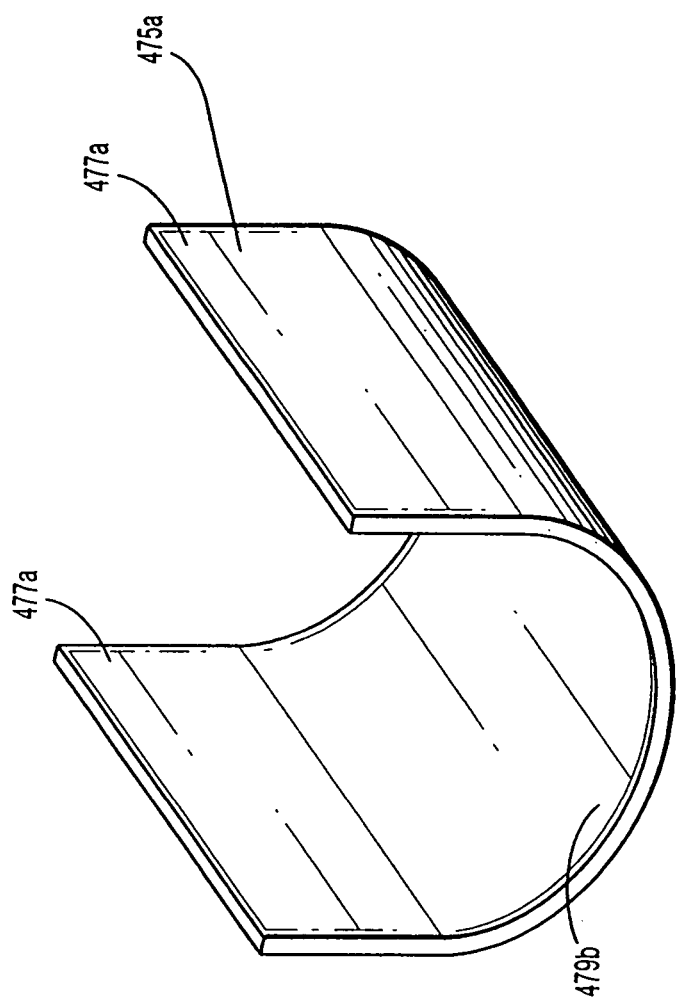
FIG. 3A is a perspective view of another compression member for use in the IV catheter.
Figure 3B:
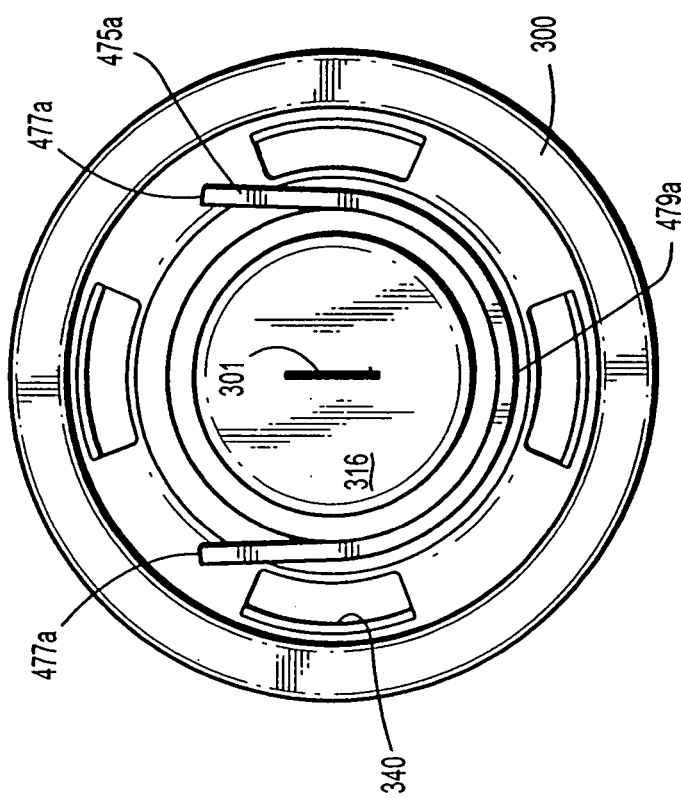
FIG. 3B is an assembled, distal cross-sectional end view of an IV catheter with the compression member of FIG. 3A in place on a septum.
Figure 4:
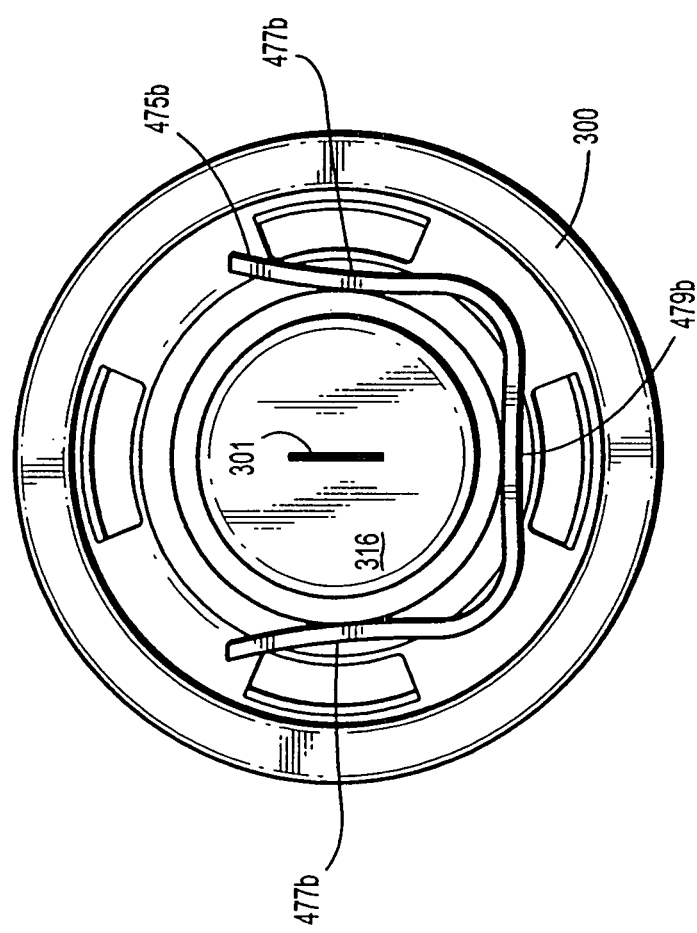
FIG. 4 is an assembled, distal cross-sectional end view of an IV catheter with still another compression member in place on a septum.

Referring to FIGS. 3A and 3B, another embodiment of a compression member 475a is shown in perspective and disposed on a septum 316, respectively. The compression device 475a is roughly U-shaped with two relatively straight legs 477a depending from an arcuate intermediate portion 479a. The legs 477a are parallel to the elongated slit 301 to provide compression substantially only perpendicular thereto. The U-shaped compression member 475a provides easier assembly and is more efficient to fabricate in certain circumstances. As one possible exemplary variation of the U-shaped member 475a, FIG. 4 shows another U-shaped member 475b having a relatively straight intermediate portion 479b, which provides even less, if any, pressure along the axis of the elongated slit 301.

Figure 5:
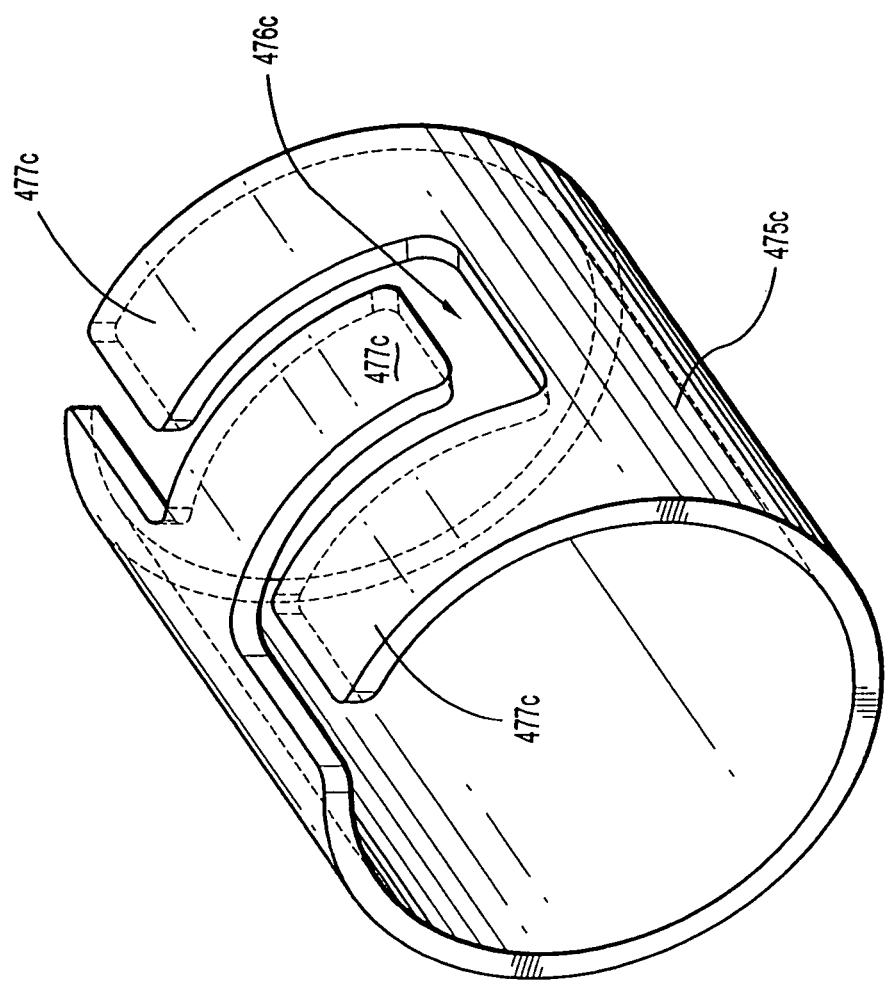
FIG. 5 is a perspective view of another compression member for use in an IV catheter.
Figure 6:
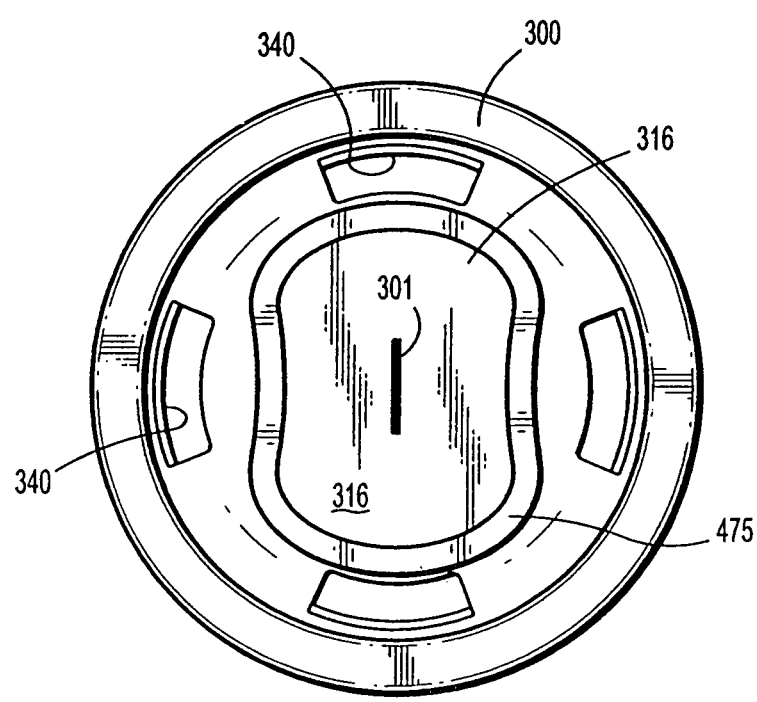
FIG. 6 is an assembled, distal cross-sectional end view of an IV catheter with another compression member in place on a septum.

Referring to FIG. 5, another embodiment of a compression member 475c is shown in perspective view. The compression member 475c is collar-shaped and defines a channel 476c that acts as an expansion joint for radial expansion and/or contraction. The channel 476c is non-linear so that interlocking legs 477c are formed. As a result of the ability to radially expand and contract, the compression member 475c is easily positioned. Upon proper placement, the compression member 475c may be crimped or squeezed for securement on the septum 316. For example, FIG. 6 shows a distal end view of a compression member 475 (e.g., 475a or 475c) that has been crimped onto a septum 316.

Figure 7:
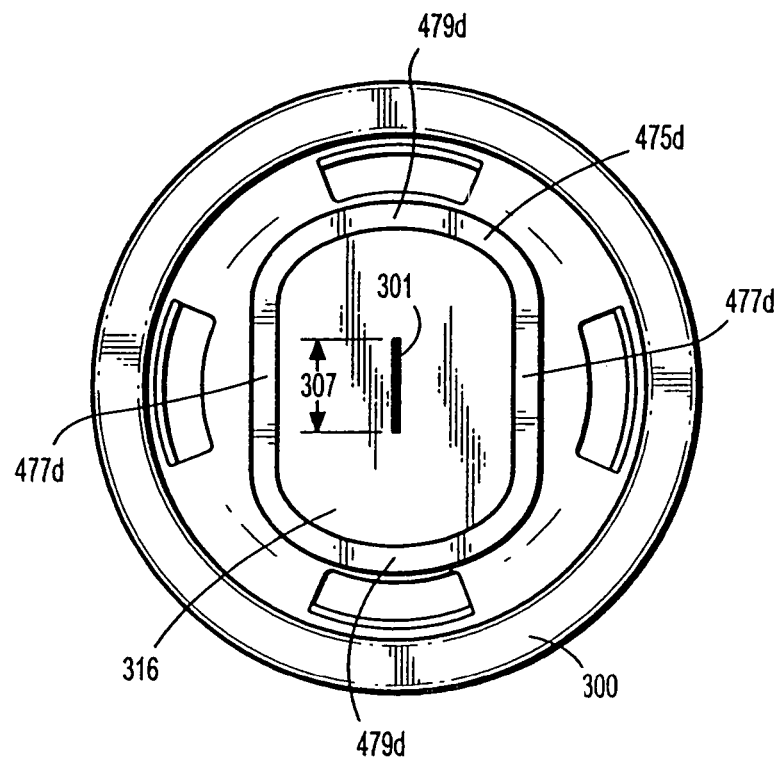
FIG. 7 is an assembled, distal cross-sectional end view of an IV catheter with still another compression member in place on a septum.
Figure 8:
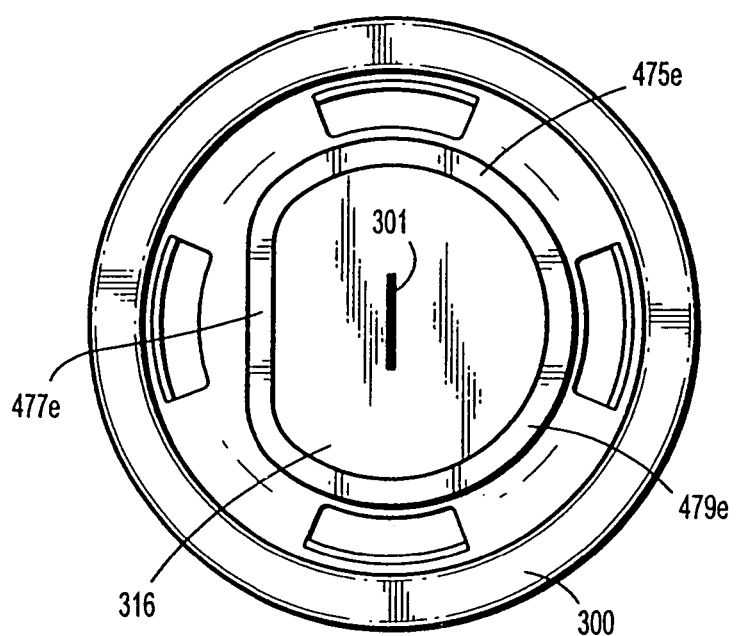
FIG. 8 is an assembled, distal cross-sectional end view of an IV catheter with still another compression member in place on a septum.

Referring to FIG. 7, another embodiment of a compression member 475d is shown disposed on the septum 316. The compression member 475d has two opposing flat sides 477d interconnected by semi-circular sections 479d such that the opposing flat sides 477d apply substantially uniform compression along the height 307 of the elongated slit 301. In other words, the septum 316 defines an elongated slit 301 having a height 307 substantially parallel to the two opposing flat sides 477d. Referring to FIG. 8, still another embodiment of a compression member 475e is shown disposed on a septum 316. The compression member 475e has a single flat portion 477e with the remainder 479e being generally arcuate. Generally, the compression members of FIGS. 6-8 are formed as collars, rings or sleeves. However, it is also envisioned that such members could be sections of wire, which may be crimped or squeezed into position on the septum.

Figure 9C:
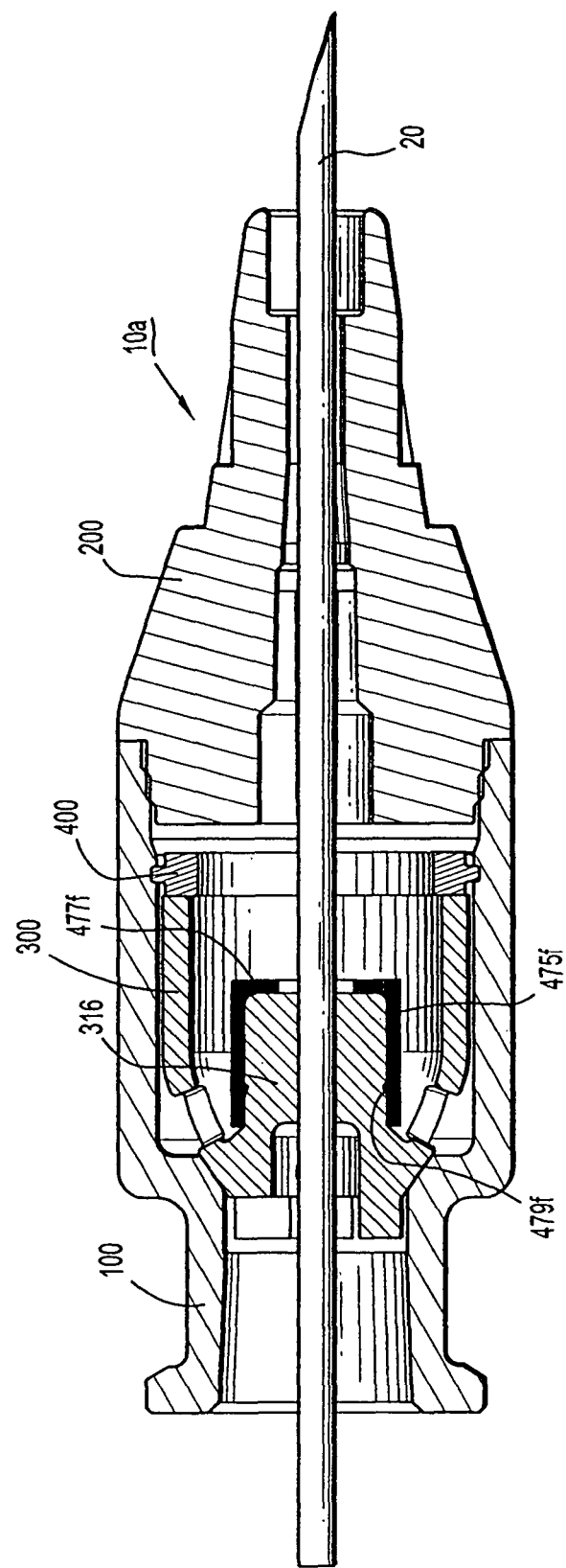
FIG. 9C is an assembled, cross-sectional, plan view of the aspect of the IV catheter of FIG. 9B with the stylet in place.

Referring now to FIG. 9A, another version of a compression member 475f is shown in a perspective view. FIGS. 9B and 9C show assembled side cross-sectional views of an IV catheter 10a with the compression member 475f before and after insertion of the stylet 20, respectively. This compression member 475f has a very similar tubular structure with that as described above but further includes a flange 477f on the distal end and one or more friction elements 479f on the inner diameter of the proximal end. When the collar 475f is disposed on the septum 316, the septum 316 is substantially within the region intermediate the flange 477f and friction elements 479f.

The flange 477f serves to facilitate proper positioning of the collar 475f by acting as an effective stop during assembly. In other words, the collar 475f is mounted onto the septum 316 until the proximal inner surface of the flange 477 is flush with the distal end of the septum 316. Since the spacing between the flange 477f and friction elements 479f and size of the septum 316 are known, such assembly assures that the septum 316 is substantially between the flange 477f and friction elements 479f. In another embodiment, the mechanism to act as a stop during assembly is one or more projections on the collar. Such projections could be as simple as a single finger-like projection, barbs or arcuate shaped projections as long as ample friction is created to prevent over-insertion of the collar.

Once properly positioned, the friction elements 479f serve to provide a retentive force on the collar 475f by creating increased friction with the seal member 300. In one embodiment, the friction elements 479f are intermittently spaced along the inner diameter of the collar 475f and may be located at the same axial location or be axially spaced with respect to each other. The friction elements 479f are sized and positioned to provide sufficient retentive force such that even a single friction element could be effective. In one embodiment, the friction elements 479f only retain the collar 475f as the collar 475f is configured to seal the septum 316 without the friction elements 479f surrounding the septum 316.

Currently it may be desirable to have both the outer surface of the septum 316 and the inner surface of collar 475f smooth, to maximize contact area between the two components. In an alternative embodiment, the friction elements are one or more raised diamond-shaped portions. In another embodiment, the friction elements comprise a roughened surface on the inner diameter of the collar so that a nominal inner diameter is present but the surface lacks smoothness and uniformity. A roughened surface on the inner diameter of the collar appears to be desirable when the septum outer surface is roughened, especially if the roughened surfaces are complementary and/or interlocking. For another example, in FIG. 10, a compression member 475g has an annular inner ring 479g to provide the retentive force with the septum 316. Various other shapes, such as a substantially circular asymmetrical ring with a plurality of substantially flattened portions, would function appropriately as would be appreciated by those of ordinary skill in the art upon review of the subject disclosure. In another embodiment, the constrictor is at least one rigid arcuate section retained against the seal member about the septum by an elastic band. In still another embodiment, compression is applied to the septum by a split ring having end portions that overlap and protrude such that upon movement of the end portion together, a diameter of the split ring increases to ease assembly. In another embodiment, compression is applied by a staple formed tightly around the septum. The staple may be various shapes adapted to compress the septum in a desirable manner such as U-shaped and the like.

Figure 10H:
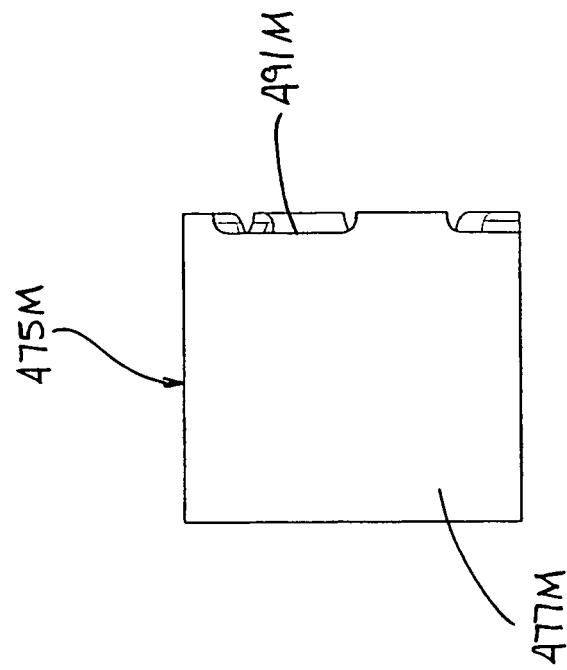
FIG. 10H is a side view of the compression member shown in FIG. 10F.

Referring to FIGS. 10A-10H, additional alternative embodiments of the compression member shown as 475H-M are disclosed. Each of compression members 475H-M includes a substantially cylindrical body defining a throughbore having retention structure formed on an inner wall of the body. Referring to FIG. 10A, compression member 475H includes a substantially cylindrical body 477H defining a throughbore 481H. Retention structure including at least one friction element 479H is formed on an internal surface 483H of body 477H. In one embodiment, the at least one friction element 479H includes a plurality of spaced ribs which define a longitudinal axis which is transverse to the longitudinal axis of body 477H. As with friction elements 479F, friction elements 479H provide a retentive force on compression member 475H by creating increased friction between internal surface 483H of compression member 475H and seal member 300 (FIG. 9B).

Referring to FIG. 10B, the at least one friction element 479I includes a plurality of spaced ribs which define a longitudinal axis which is transverse to the longitudinal axis of body 477I of compression member 475I. Friction elements 479I differ from friction elements 479H in that each end of each friction element 479I includes a pointed, e.g., triangular, protrusion 485I. The configuration of the protrusion 485I increases the retention force of the friction elements.

Referring to FIG. 10C, the at least one friction element 479J includes a plurality of spaced pointed or triangular protrusions positioned on internal surface 483J of compression member 475J. The apex of each friction element 479J is directed outwardly to press into septum 316 (FIG. 9B). In FIG. 10D, the at least one friction element 479K includes a plurality of triangular protrusions positioned on internal surface 483K of compression member 475K. A base 485K of friction elements 479K is positioned on septum 316 to face distally to oppose removal of compression member 475K from a septum. In FIG. 10E, the at least one friction element 479L includes a plurality of rectangular protrusions positioned on internal surface 483L of compression member 475L. Although shown on the distal end of compression member 475L, friction elements 479L may be provided on the proximal end of compression member 475L or between the proximal and distal ends of the compression member 475L.

Referring to FIGS. 10G-10H, compression member 475M includes a substantially cylindrical body 477M defining a throughbore 481M. A plurality of spaced friction elements 479M are positioned about an internal surface of body 477M. Friction elements 479M are in the form of angled barbs which extend in a distal direction and include an apex 487M and a sloped proximal surface 489M. Sloped proximal surfaces 489M allow compression member 475M to be slid over and about a septum 316 (FIG. 9B) while apexes 487M of the barbs substantially prevent removal of compression member 475M from septum 316.

Figure 10F:
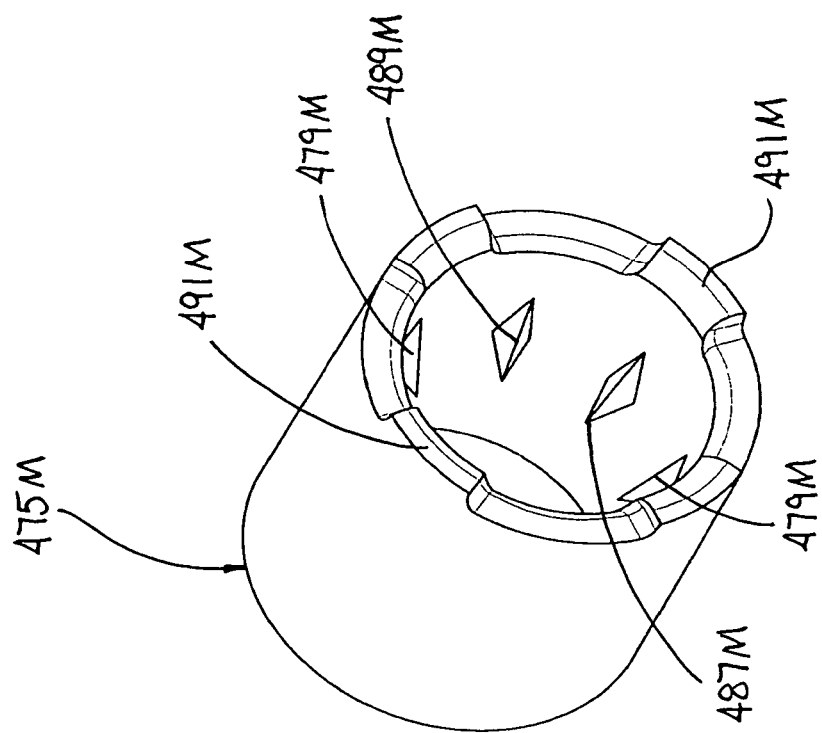
FIG. 10F is a perspective view of another compression member for use with an IV catheter.

As illustrated in FIGS. 10F and 10H, a proximal end of body 477M of compression member 475M includes indicia in the form of one or more cutouts 491M or tabs 493M. Cutouts 491M and/or tabs 493M provide a visual indication to a manufacturer that the compression member is properly oriented for placement on a septum and/or that a compression member has been properly positioned on a septum. More specifically, cutouts 491M and/or tabs 493M are configured to identify the distal end of the compression member such that prior to placement of the compression member onto a septum, a manufacturer can, visually or with the use of automated equipment, confirm that the compression member is properly oriented. Cutouts 491M and/or tabs 492M may also be positioned on compression member 475M such that when compression member 475M is properly positioned on a septum 316, cutouts 491M and tabs 493M are positioned on a distal end of septum 316 and tabs 493M are flush with a distal face of septum 316. This visual indication may be done by eye or, alternatively, by a mechanical and/or electrical inspection apparatus. Although four rectangular cutouts are illustrated, one or more cutouts of any desired configuration may be used, e.g., circular, trapezoidal, square, etc. Alternatively, other indicia including protrusions, color coding, etching, etc. may be provided to identify to a manufacturer that the compression member has been properly positioned on septum 316 (FIG. 9B).

Although each of the compression members described above includes a plurality of friction elements, it is envisioned that one or more friction elements may be provided. The one or more friction elements may be located at any location on the internal surface of the compression member between the proximal and distal ends of the compression member.

Figure 11:
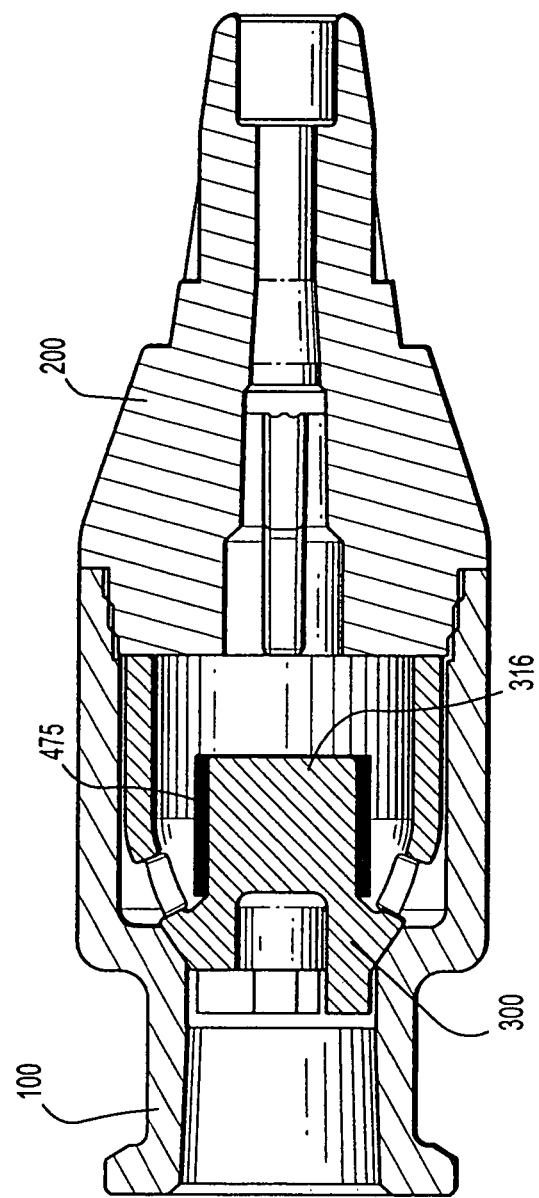
FIG. 11 is an assembled, cross-sectional view of an IV catheter having a two-piece housing with the compression member in place.

It is also envisioned that various compression members may be deployed with different septums and housings. For example, in FIG. 11 the IV catheter does not have a locking ring member 400, i.e., the IV catheter is a two-piece housing design including the proximal housing 100 and the distal housing 200 that are secured to each other so as to form an integral unit and so as to form a pressure boundary.

Figure 12A:
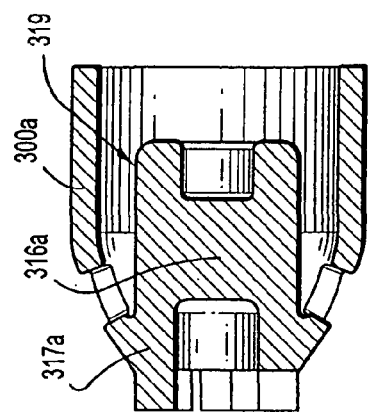
FIG. 12A is a cross-sectional view of another seal member with a remote septum for use in an IV catheter.
Figure 12B:
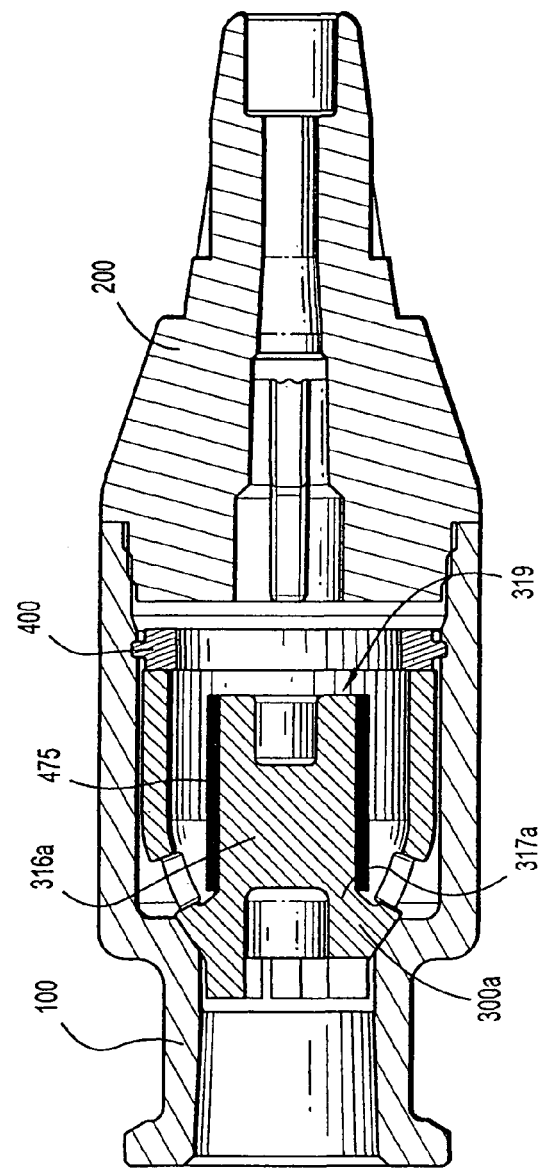
FIG. 12B is an assembled, cross-sectional, plan view of an IV catheter with the compression member of FIG. 2F in place.
Figure 12C:
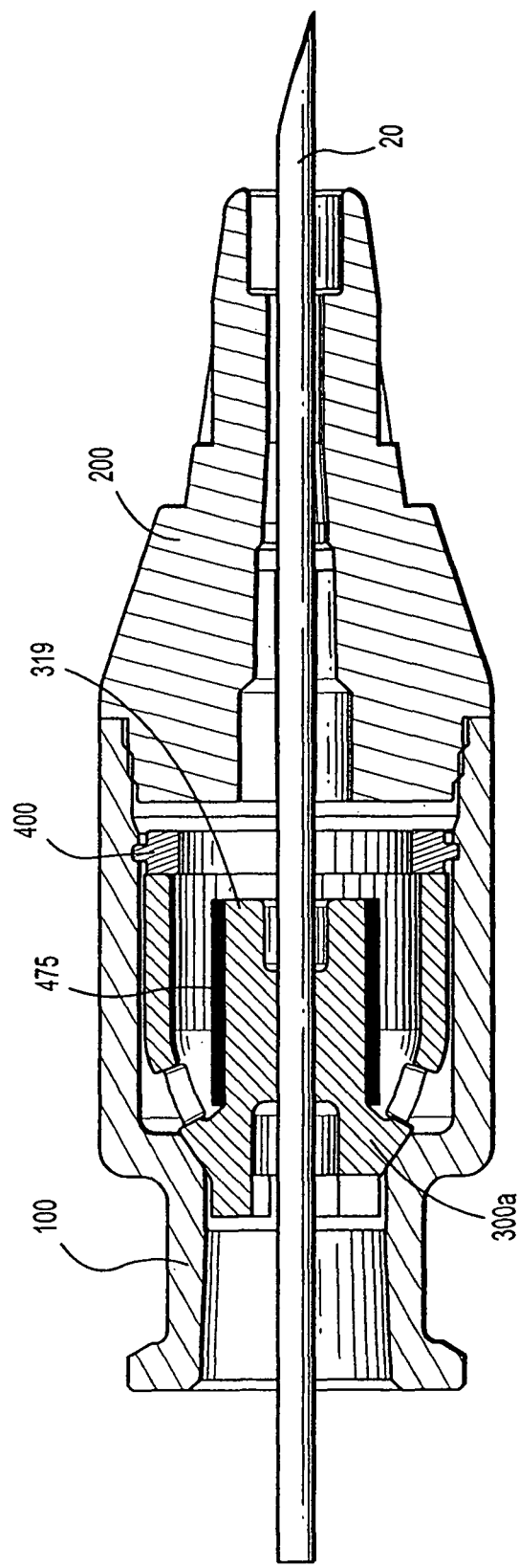
FIG. 12C is an assembled, cross-sectional, plan view of the aspect of the IV catheter of FIG. 12B with the stylet in place.

In FIG. 12A, another seal member 300a for use with a septum collar 475 is shown in cross-sectional view. Side wall(s) 317a extends beyond the septum 316a so as to create a collar portion 319 that extends outwardly from and beyond the septum 316a. Without being bound to any particular theory or principle of science, the collar portion 319 enhances the ability of the septum 316a to self-close or self-seal itself after the insertion stylet/sharp/cannula 20 is removed from the septum 316a. In FIGS. 12B and 12C the seal member 300a is shown assembled in an IV catheter with and without the stylet 20, respectively.

Figure 13A:
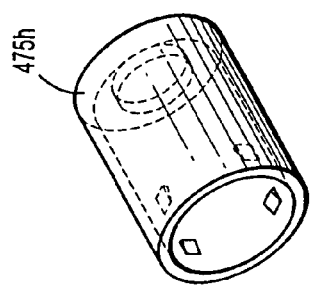
FIG. 13A is a perspective view of yet another compression member for use in an IV catheter.
Figure 13B:
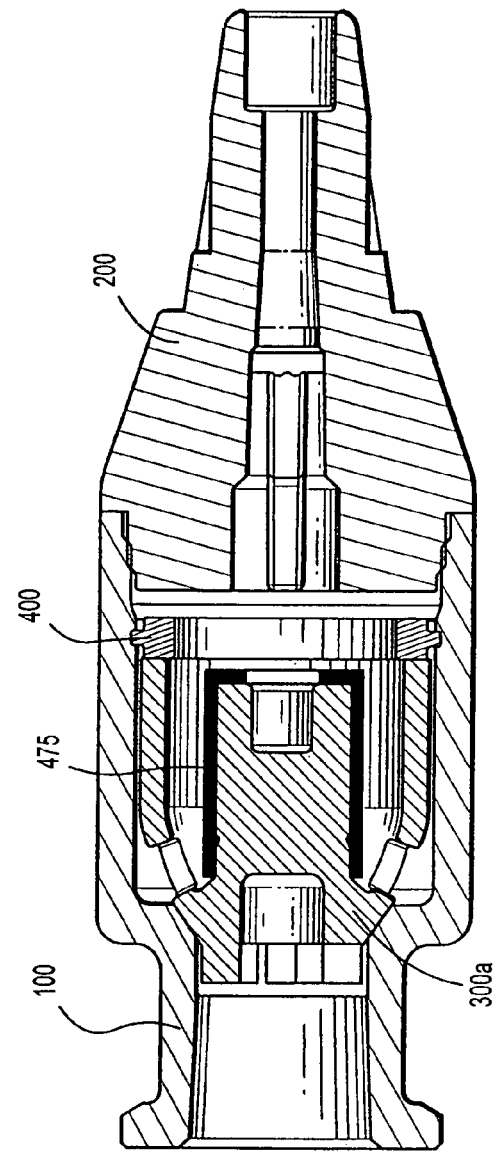
FIG. 13B is an assembled, cross-sectional, plan view of an IV catheter with the compression member of FIG. 13A in place.
Figure 13C:
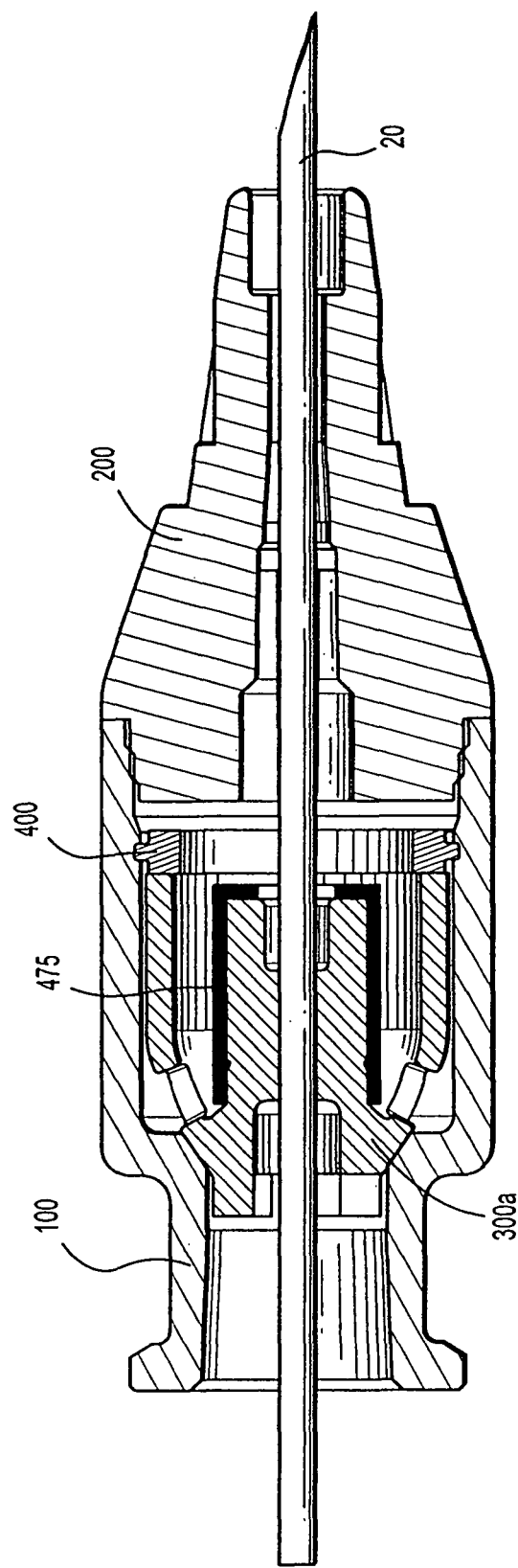
FIG. 13C is an assembled, cross-sectional, plan view of the aspect of the IV catheter of FIG. 13B with the stylet in place.

In FIG. 13A, another version of a compression member 475h is shown in a perspective view for use with a seal member 300a such as shown in FIG. 12A. FIGS. 13B and 13C show assembled side cross-sectional views of an IV catheter 10h with this compression member 475h before and after insertion of the stylet 20, respectively. This compression member 475h has a very similar structure with that as described above with respect to compression member 475f.

Figure 14:
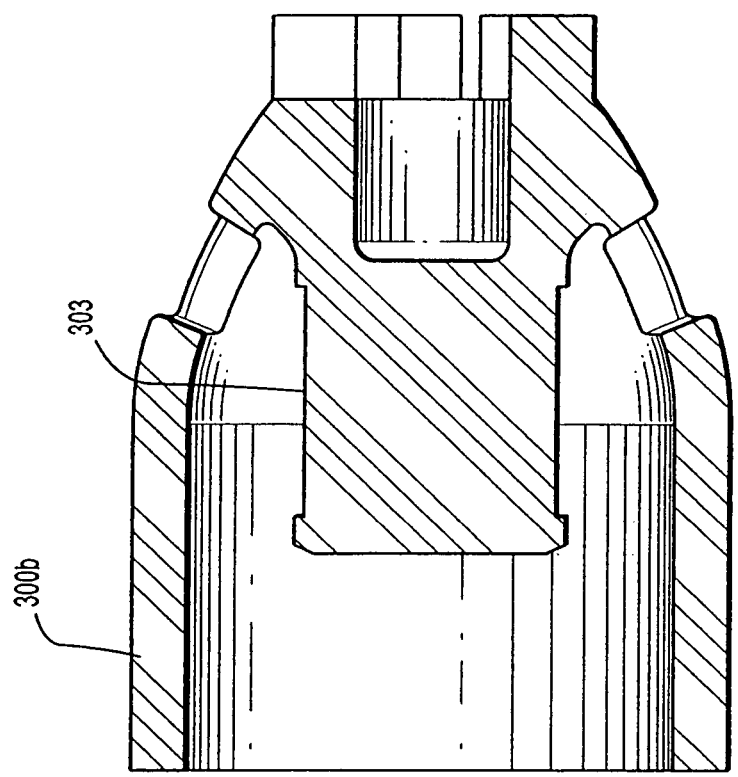
FIG. 14 is a cross-sectional view of yet another seal member with a remote septum for use in an IV catheter.

Still another embodiment of a seal member 300b is shown in cross-sectional view in FIG. 14. The primary difference of this seal member 300b is an annular groove 303 for receiving a compression member (not shown). In another embodiment, the seal member is configured so as to include an outer annular ridge that is disposed about the septum to enlarge a radius thereof approximate the point of compression by the compression member. In another embodiment, the septum extends axially along the stylet in one or more directions. The septum may also form a pre-set axial passageway. The passageway may be symmetrical or asymmetrical such as, without limitation, a tapered slit with a relatively smaller proximal end. It is also envisioned, without limitation, that the compression member may be a plurality or combination of items such as a crimped ring, at least one rigid arcuate section retained against the septum by an elastic band, a split ring having end portions that overlap and protrude such that upon movement of the end portion together, a diameter of the split ring increases, and/or a U-shaped staple prior to placement, wherein upon placement each end of the staple is formed tightly around the septum.

Figure 14A:
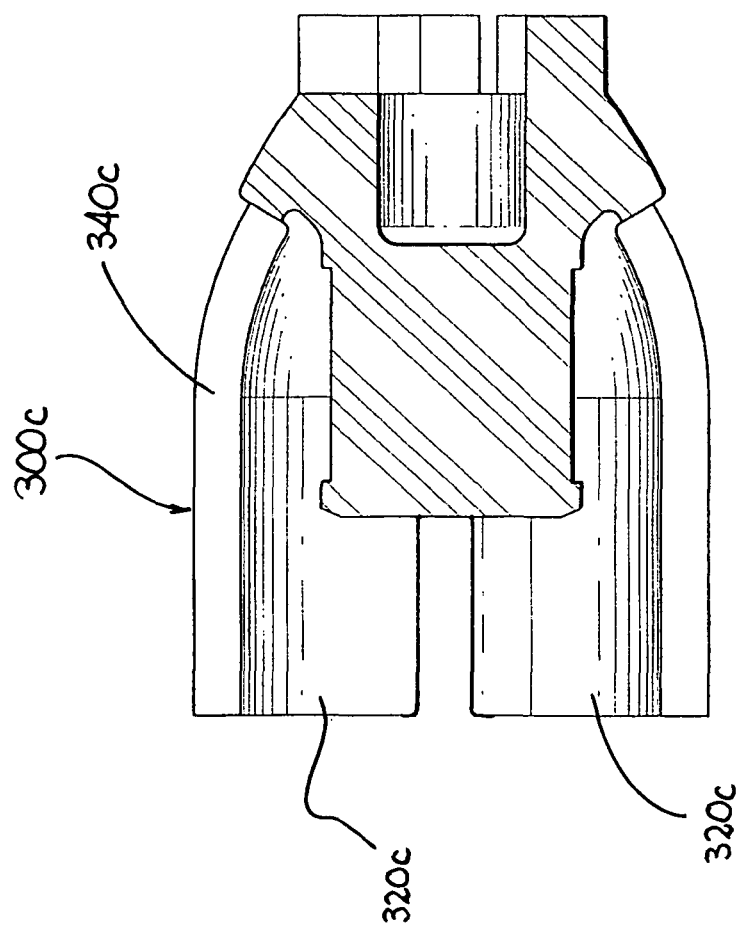
FIG. 14A is a cross-sectional view of another embodiment of the presently disclosed seal member.

FIG. 14A illustrates still another embodiment of a seal member 300c shown in cross-section. Seal member 300c is similar to seal 300b except that the seal member windows have been extended distally to define a plurality of spaced channels 340c. Each of channels 340c is separated by a leg portion 320c of seal member 300c.

It should be noted that it is contemplated, and thus within the scope of the present invention, for the subject invention to further comprise device kits that include one or more of the in-line valve IV catheters and which device kits maintain the in-line valve IV catheter in sterile conditions during shipment from the manufacturing facility and in storage prior to use. Such device kits also can further include other instrumentalities, devices or materials normally associated with use of the catheter, including but not limited to tubing, cleaning materials to establish aseptic conditions prior to insertion of the IV catheter and/or clips/clamps or the like for regulating flow of fluid from an IV drip to the patient.

Figure 15B:
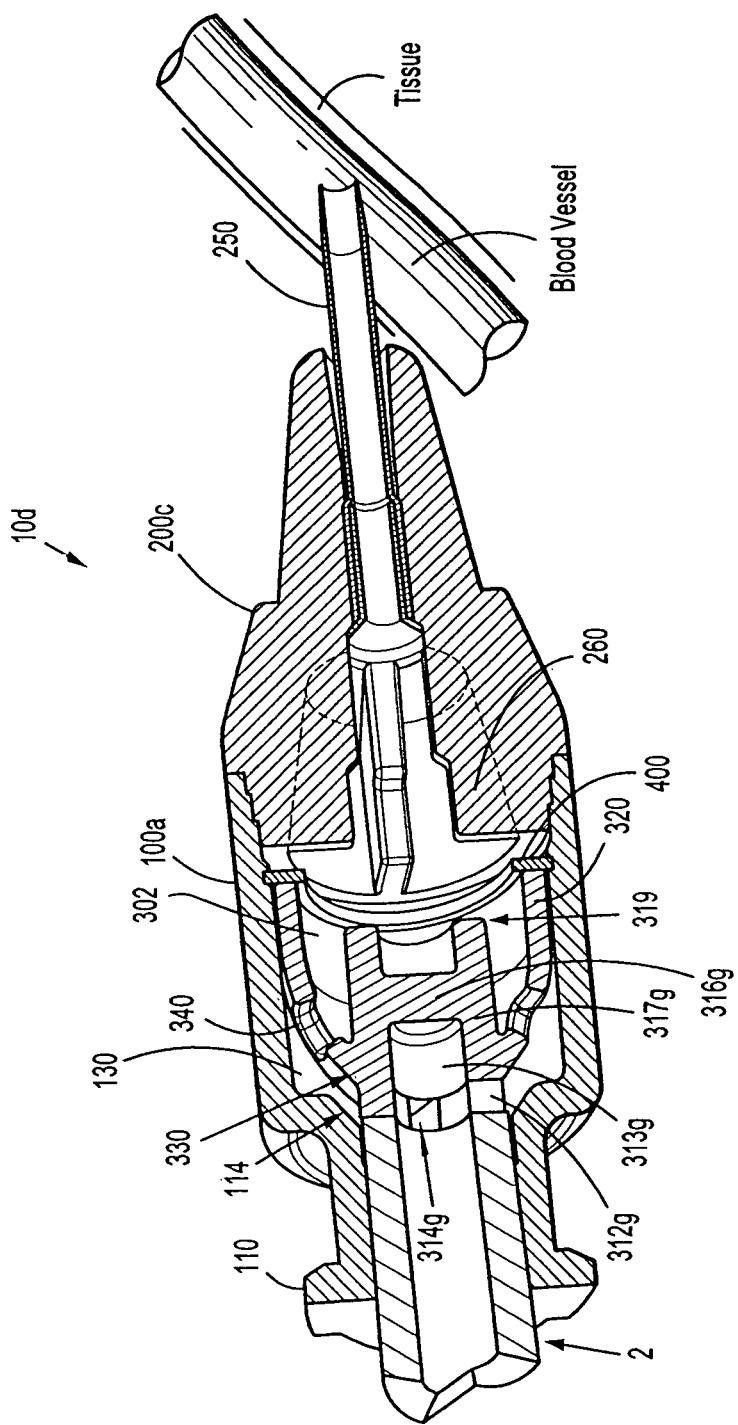
FIG. 15C is an annotated cross-sectional view of the in-line valve IV catheter of FIG. 11B illustrating fluid flow in one direction when the sealing portion of the seal member is displaced responsive to the insertion of a nose of a luer device.
Figure 15C:
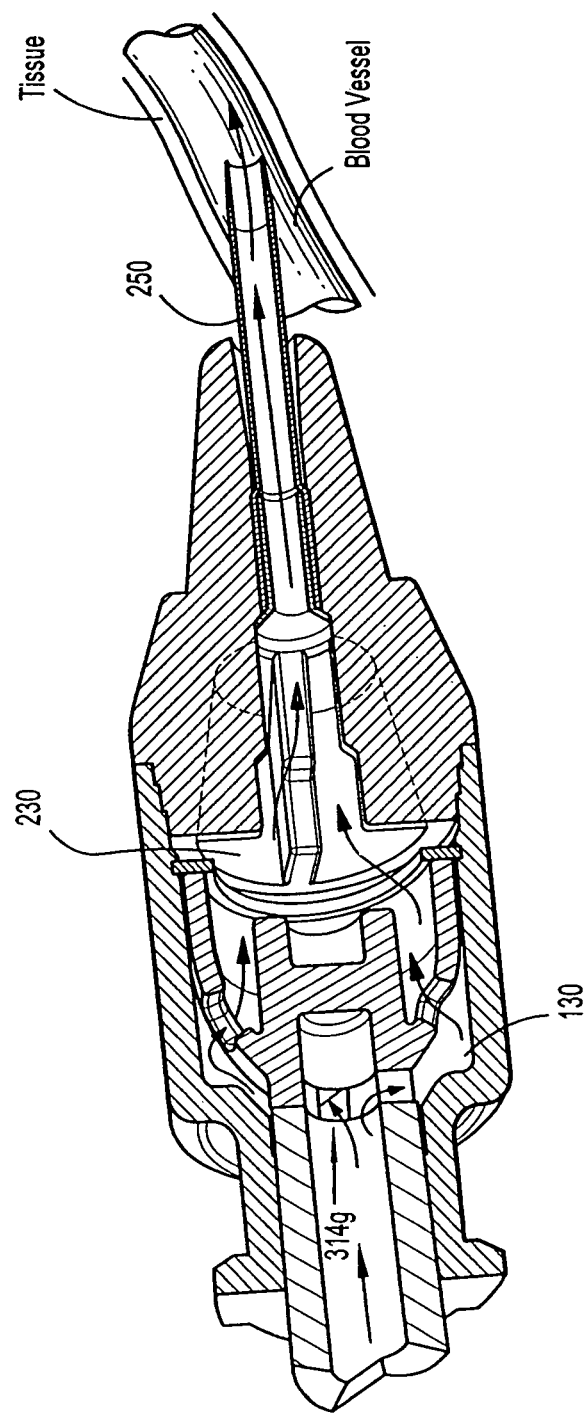

Referring to FIGS. 15A-C, cross-sectional views of the in-line valve IV catheter illustrating an exemplary use and fluid flow of such an IV catheter are illustrated. Reference shall be made to U.S. Provisional Patent Application No. 60/726,026, filed Oct. 11, 2005, and the foregoing discussion regarding details or characteristics regarding the IV catheter not otherwise described or detailed herein. Additionally, although not shown, a compression member, as discussed above, could be advantageously used about the septum 316g.

Initially, the medical personnel would prepare the in-line valve IV catheter 10d for use in accordance with the procedure to be performed including removing the catheter from any device kit. The medical personnel would then perform the usual and customary actions to identify a potential target insertion site (e.g., locating a vein in which the open end of the tubular member 250 would be located) and to prepare the exposed skin of the patient surrounding the injection site for insertion of the needle into the patient's skin. Such preparing can include, for example, performing a cleaning and/or sterilizing operation (e.g., swabbing the skin with alcohol swab, applying a sterilizing solution).

Thereafter, the medical personnel would locate the sharp end 22 or point of the introducer needle 20 on the patient's body at the target insertion site. Following such localizing, the medical personnel would insert the sharp end 22 or point of the introducer needle 20 into and through the skin of the patient and the wall of the blood vessel such that the needle sharp end resides within the targeted blood vessel of the patient as shown in FIG. 15A.

As indicated herein, once the sharp end 22 of the introducer needle 20 is in the blood vessel, the pressure of the blood within the patient causes blood to flow back or flashback in a proximal direction through the lumen in the introducer needle to the flashback chamber or a needle hub or space between the needle and catheter. In accordance with accepted practices, if the medical personnel observe such blood flashback in the flashback chamber it is concluded that the open end of the tubular member also resides in the blood vessel. It should be noted that if the medical personnel do not observe such blood flashback, the medical personnel again attempt to insert the needle into the target vein and/or identify a new target vein and repeat to the extent necessary any of the foregoing steps (e.g., repeat the process if the new target vein is in another location or body part).

If it is determined that the needle end 22 is in the blood vessel/vein, the medical personnel then take the appropriate actions to remove the introducer needle 20 from the in-line IV catheter 10d. Typically, the medical personnel would grasp a handle, the flashback chamber or other mechanism of the related structure of the introducer needle 20 and draw the needle in a proximal direction thereby drawing the sharp end of the needle through and thence out of the in-line IV catheter. After the introducer needle 20 is removed from the in-line valve IV catheter 10d, the catheter remains positioned in the blood vessel (i.e., the open end thereof is within the blood vessel). It should be noted that after such removal or in conjunction with such removal, a needle end protection device can be actuated to protect users from the needle's sharp end 22, thereby preventing accidental needle sticks, such as, for example, the safety shield devices described in PCT Publication No. WO 2005/042073 published May 12, 2005. In addition, the medical personnel can advance the in-line valve IV catheter 10d deeper into the vein by pushing gently on the coupling end 110 of the proximal housing 100 as the catheter is being advanced off the introducer needle 20 to arrive at the orientation shown in FIG. 15B.

At this point, the in-line valve IV catheter 10d is now positioned within the vein as a completely enclosed direct luer vascular access system ready to receive a luer end such as for a syringe or an IV tubing system. The in-line valve IV catheter 10d of the present invention thus allows immediate luer access to the blood vessel of the patient for infusion of medication or blood collection utilizing a blood collector having a luer tip as are known in the art.

Referring now also to FIG. 15C, in which is shown an annotated cross-section view illustrating fluid flow in the distal direction; when the in-line valve IV catheter 10d is configured in the valve open configuration, fluid is free to flow from the coupling connection 110 through the channels 314g in the seal member proximal end 310, about the seal member 300 in a portion of the proximal housing inner cavity 130 and thence through the windows 340 of the seal member. The fluid continues to flow through the seal member inner cavity 302, through the aperture or opening in the locking ring member 400, through the distal chamber inner cavity 230, through the lumen in the tubular member 250 and thence into the blood vessel. The converse would apply if the fluid was to flow in the proximal direction such as in the case where fluid was being extracted from the blood vessel such as for sampling for diagnostic testing.

When the male luer is detached or decoupled from the coupling connection 110 of the proximal housing 100, the axial force displacing the sealing portion 330 of the seal member is no longer being applied to the seal member proximal end 310. As herein described, when the axial force is removed, the resiliency of the seal member 300 causes the proximal portion 310 thereof to move proximally and axially so as to cause the sealing portion 330 to again sealingly engage the seating surface 114 of the proximal housing. Thus, the in-line valve IV catheter 10d is restored or returned to the valve closed condition.

When the in-line valve IV catheter 10d is no longer needed, the medical personnel, using appropriate techniques, would remove the tubular member 250 from the blood vessel and tissues of the patient.

Figure 16:
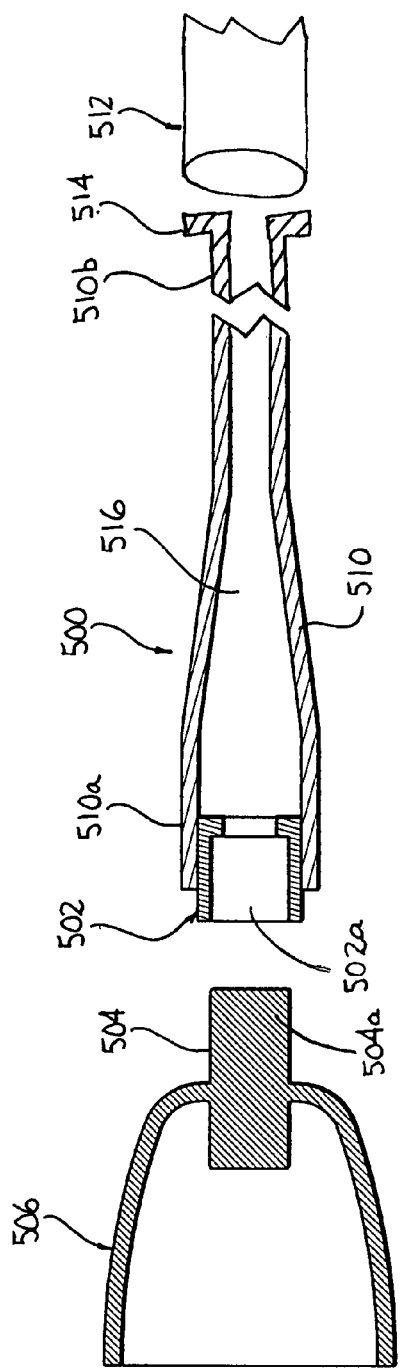
FIG. 16 is a side cross-sectional view of a vacuum system for positioning a compression member about the septum of a seal member.

FIG. 16 illustrates an apparatus 500 for positioning a compression member 502 about a septum 504 of a seal member 506. Although seal member 506 and compression member 502 are shown to have a specific configuration, apparatus 500 can be used to position any compression member, including those previously described herein, about the septum of any sealing member, including those previously described herein.

As illustrated in FIG. 16, apparatus 500 includes a vacuum conduit 510 and a source 512 of low pressure or vacuum. Vacuum conduit 510 has a first end 510a configured to sealingly engage one end of compression member 502 and a second end 510b which is adapted to communicate with source 512 of low pressure or vacuum. Second end 510b can include engagement structure 514 for securing vacuum conduit 510 to source 512. Engagement structure 514 can include threaded couplings, luer connectors, snap connectors or the like. It is also envisioned that conduit 510 can be integrally attached to a portion of source 512. As illustrated, conduit 510 defines a fluid channel 516 which interconnects source 512 to first end 510a of conduit 510.

In use, compression member 502 is supported within first end 510a of conduit 510 such that the open end 502a of compression member 502 which is dimensioned and configured to receive septum 504 of seal member 506 is facing outwardly of conduit 510. It is envisioned that a support member can be provided on first end 510a of conduit 510 to engage and hold compression member 502. Compression member 502 can be fictionally retained within end 510a of conduit 510, e.g., conduit 510 can be in the form of a flexible tube or hose which can be stretched to receive compression member 502. Alternatively, additional clamps or ties, not shown, can be provided about first end 510a of conduit 510 to secure compression member 502 within conduit 510. After compression member 502 is secured within first end 510a of conduit 510, vacuum source 512 is operated to create a low pressure area within compression member 502. Thereafter, distal end 504a of septum 504 is positioned into open end 502a of compression member 502. The pressure differential on the opposite sides of septum 504 urges or draws distal end 504a of septum 504 into opening 502a of compression member 502 to position compression member 502 about septum 504 of seal member 506.

Figure 17:
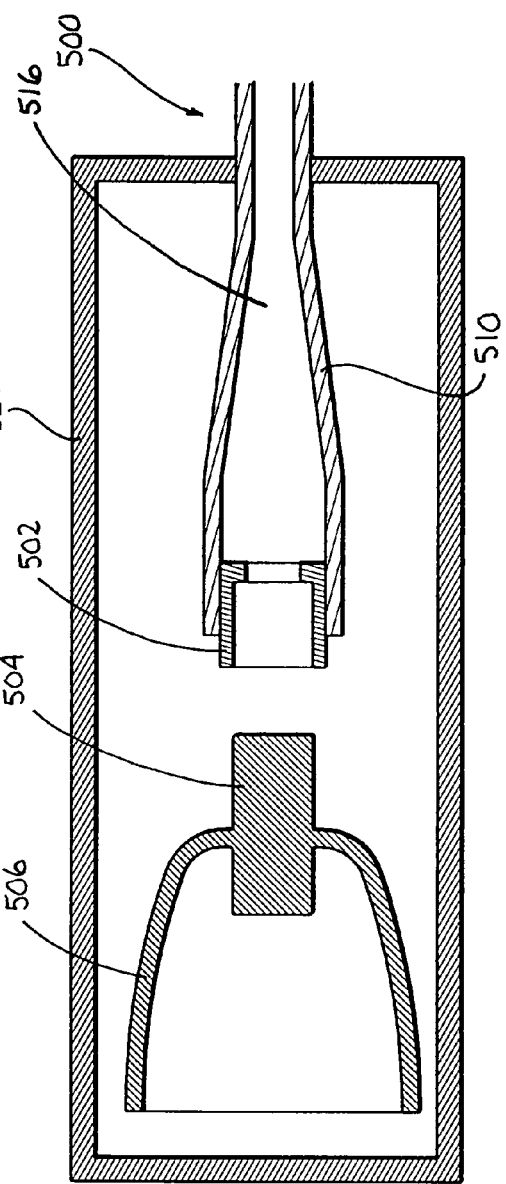
FIG. 17 is a side cross-sectional view of the vacuum system shown in FIG. 16 in combination with a pressurized enclosure for positioning a compression member on the septum of a seal member.

Referring to FIG. 17, a pressurized chamber 520 has been provided to provide a greater pressure differential across septum 504 of seal member 506 to further assist in positioning distal end 504a of septum 504 into compression member 502. More specifically, if atmospheric is 14.7 psi and the pressure within channel 516 is O psi, the pressure differential across septum 504 is 14.7 psi. By providing a pressurized chamber 520 in which the pressure is increased above atmospheric pressure to, for example, 25 psi, the pressure differential across septum 504 is increased to 25 psi. By increasing the pressure differential across septum 504, a greater force is provided to urge septum 504 into compression member 502.

Although not shown herein, a lubricant can be provided on distal end 504a of septum 504 or along the inner walls of compression member 502 to further assist in positioning compression member 502 about septum 504 of seal member 506.

In an alternative embodiment, a molding apparatus (not shown) is provided to allow the septum of the seal member to be insert molded within the compression member. By molding the septum within the compression member, the manufacturing step of assembling the compression member and septum of the seal member is eliminated to simplify the manufacturing process. In one embodiment, the mold material used to mold the septum within the compression member expands as it cures or cools within the compression member. As a result, the molded septum is supported in compression by the compression member. The molding process described herein can be adapted to mold the septum of any of the previously described seal members within any of the previously described compression members.

Figure 18:
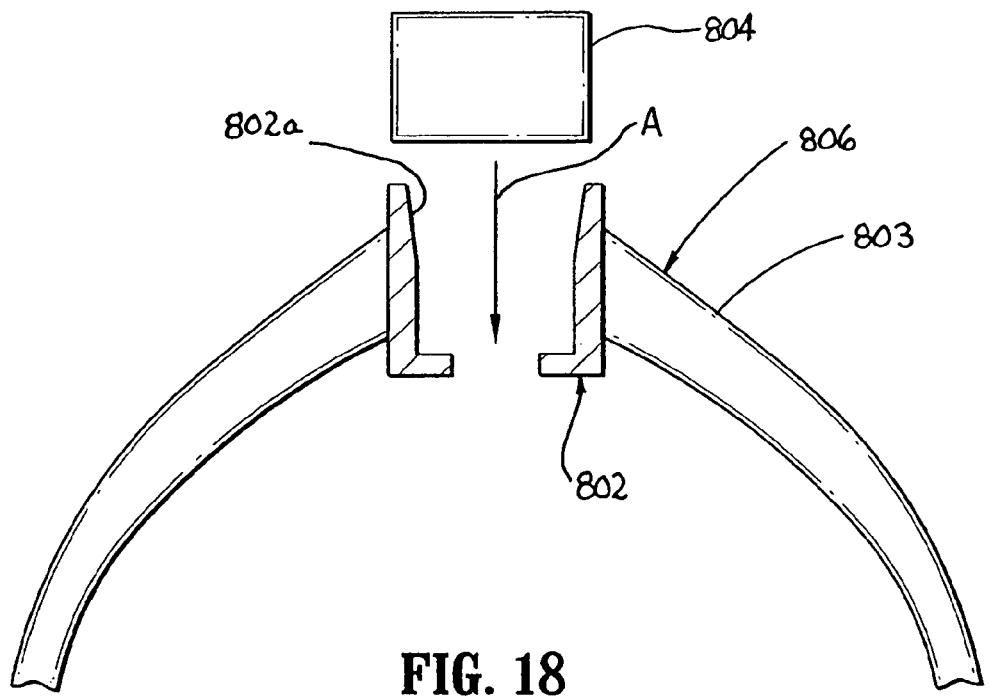
FIG. 18 is a side cross-sectional view of another embodiment of the presently disclosed seal member and compression member during insertion of the seal member septum into the compression member from the exterior of the seal member.
Figure 19:
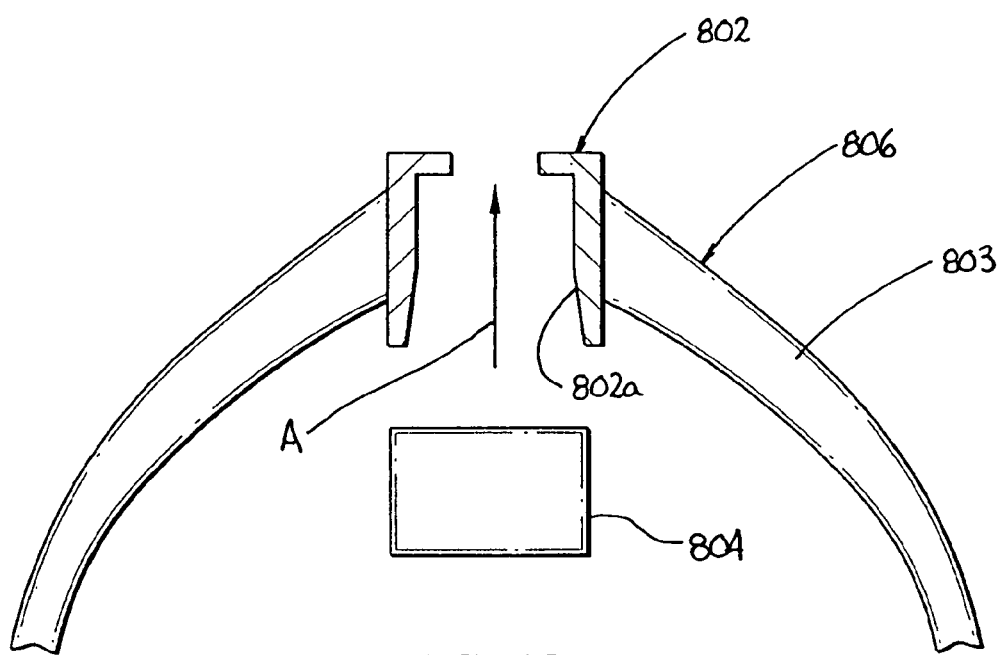
FIG. 19 is a side-cross-sectional view of another embodiment of the presently disclosed seal member and compression member during insertion of the seal member septum into the compression member from the interior of the seal member.
Figure 20:
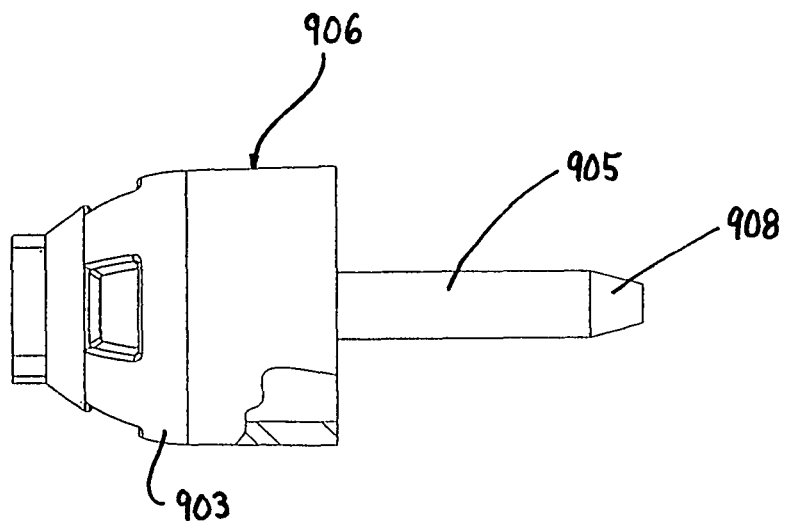
FIG. 20 is a side view of another embodiment of the presently disclosed seal member.

In another embodiment shown in FIGS. 18 and 19, a bell portion 803 of seal member 806 is molded to and about compression member 802. Thereafter, septum 804 can be pressed in the direction indicated by arrow "A" into compression member 802. The septum receiving end of compression member 802 can include an outwardly tapered inner surface 802a to facilitate insertion of septum 804 into compression member 802. As illustrated in FIGS. 19 and 20, compression member 802 can be molded to bell portion 803 to receive septum 804 from within bell portion 803 (FIG. 19) or, alternatively, from exteriorly of bell portion 803 (FIG. 18).

Figure 21:
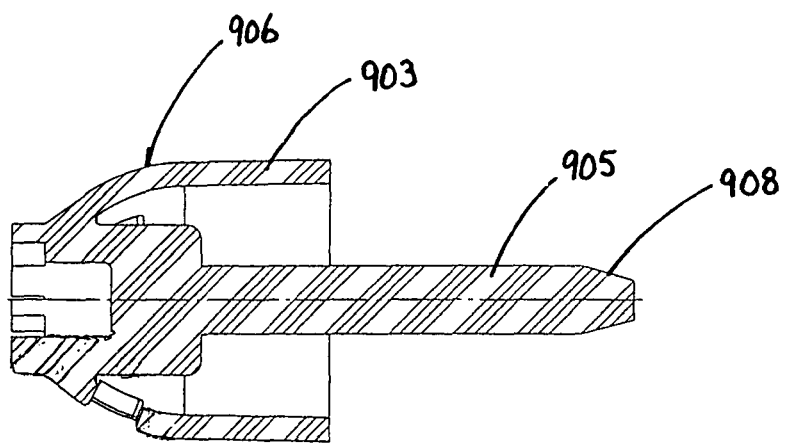
FIG. 21 is a side cross-sectional view of the seal member shown in FIG. 19.

In yet another embodiment, shown in FIGS. 20 and 21, seal member 906 includes a bell portion 903, a septum 904, and a tab or extension 905 extending distally from septum 904. Tab 905 is preferably aligned with the longitudinal axis of septum 904 and has a diameter which is smaller than the diameter of septum 904. The smaller diameter of tab 905 is dimensioned to easily pass through the hollow compression member (see, e.g., compression member 802 in FIG. 18) to facilitate positioning of the compression member about septum 904. A chamfer or bevel 908 positioned at the distal end of tab 905 assists insertion of tab 905 through the opening in the compression member. More specifically, the compression member is slid over tab 905 of seal member 906 to a position adjacent septum 904. Thereafter, the compression member is held, e.g., in one band, and tab 905 is pulled, e.g., with the other hand, to pull septum 904 into the hollow compression member. Although illustrated as being cylindrical, tab 905 may assume a variety of different configurations, e.g., rectangular, plate-like, etc.

In one embodiment, tab 905 is separated from seal member 902, such as by cutting, after the compression member is positioned about septum 904 and does not form part of the IV Catheter In-Line Valve. Alternatively, tab 905 can be provided with an opening (not shown) which is contiguous with an opening in septum 904 to facilitate passage of an object, e.g., an introducer needle, insertion cannula or the like, through septum 904 and tab 905.

Figure 22:
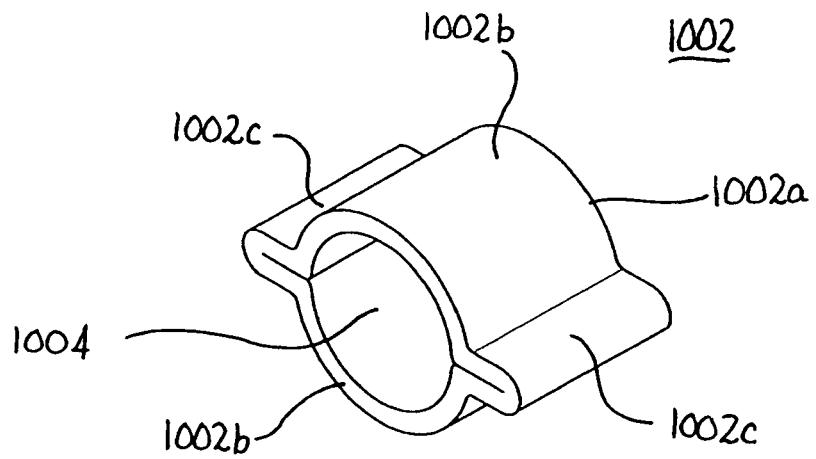
FIG. 22 is a side perspective view of another embodiment of the presently disclosed compression member in a crimped configuration.
Figure 23:
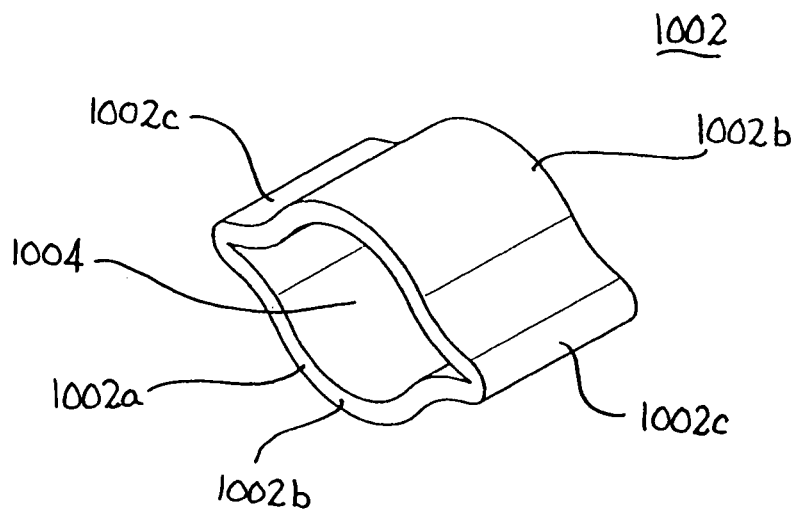
FIG. 23 is a side perspective view of the compression member shown in FIG. 22 prior to being crimped.

FIGS. 22 and 23 illustrate another embodiment of the presently disclosed compression member shown generally as 1002. Compression member 1002 is substantially eye-shaped in its uncrimped configuration (FIG. 23) and includes a body 1002a having circular upper and lower body portions 1002b which are interconnected by and converging end portions 1002c. The uncrimped compression member 1002 (FIG. 23) defines a throughbore 1004 dimensioned to easily receive a septum of a seal member. After compression member 1002 has been positioned about the septum of a seal member, end portions 1002c are crimped using any known crimping tool (not shown) to compress compression member about the septum of the seal member (FIG. 22). It is envisioned that compression member 1002 can be dimensioned to provide varying degrees of compression to the septum of the seal member. For example, compression member 1002 (or any of the compression members disclosed herein) can be dimensioned to provide compression to the septum prior to insertion of a device through the septum, or only after insertion of a device through the septum.

Figure 24:
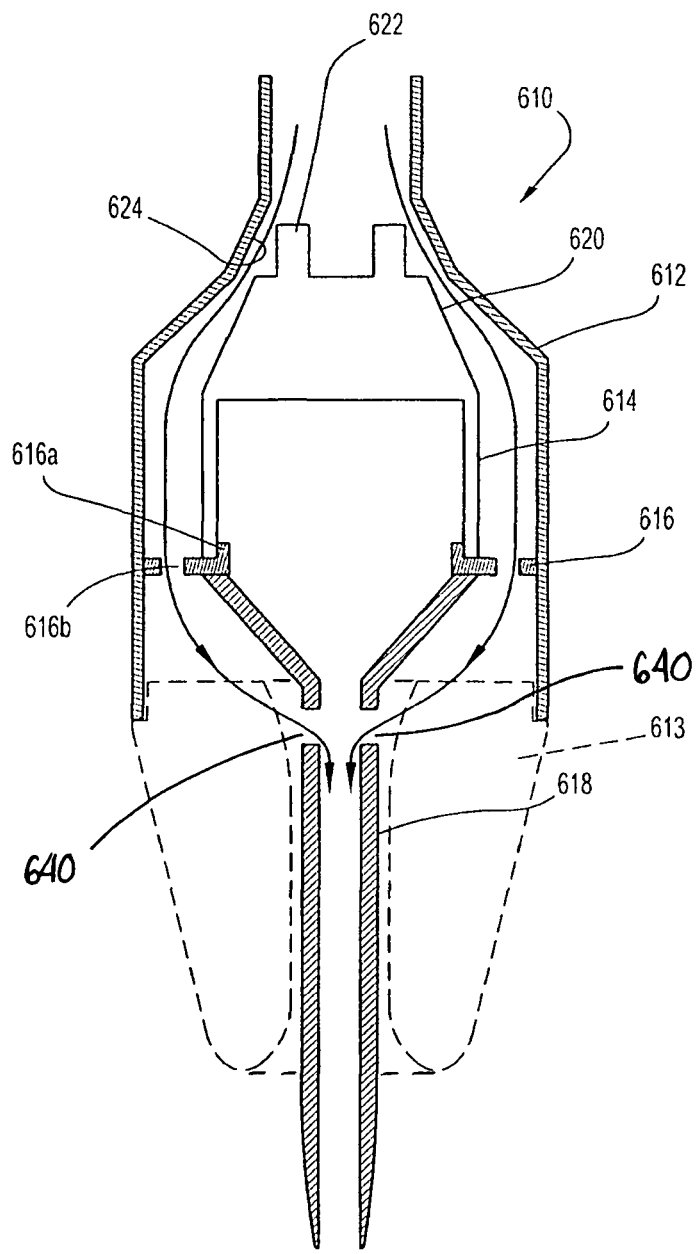
FIG. 24 is a side cross-sectional view of another embodiment of the presently disclosed IV catheter.
Figure 25:
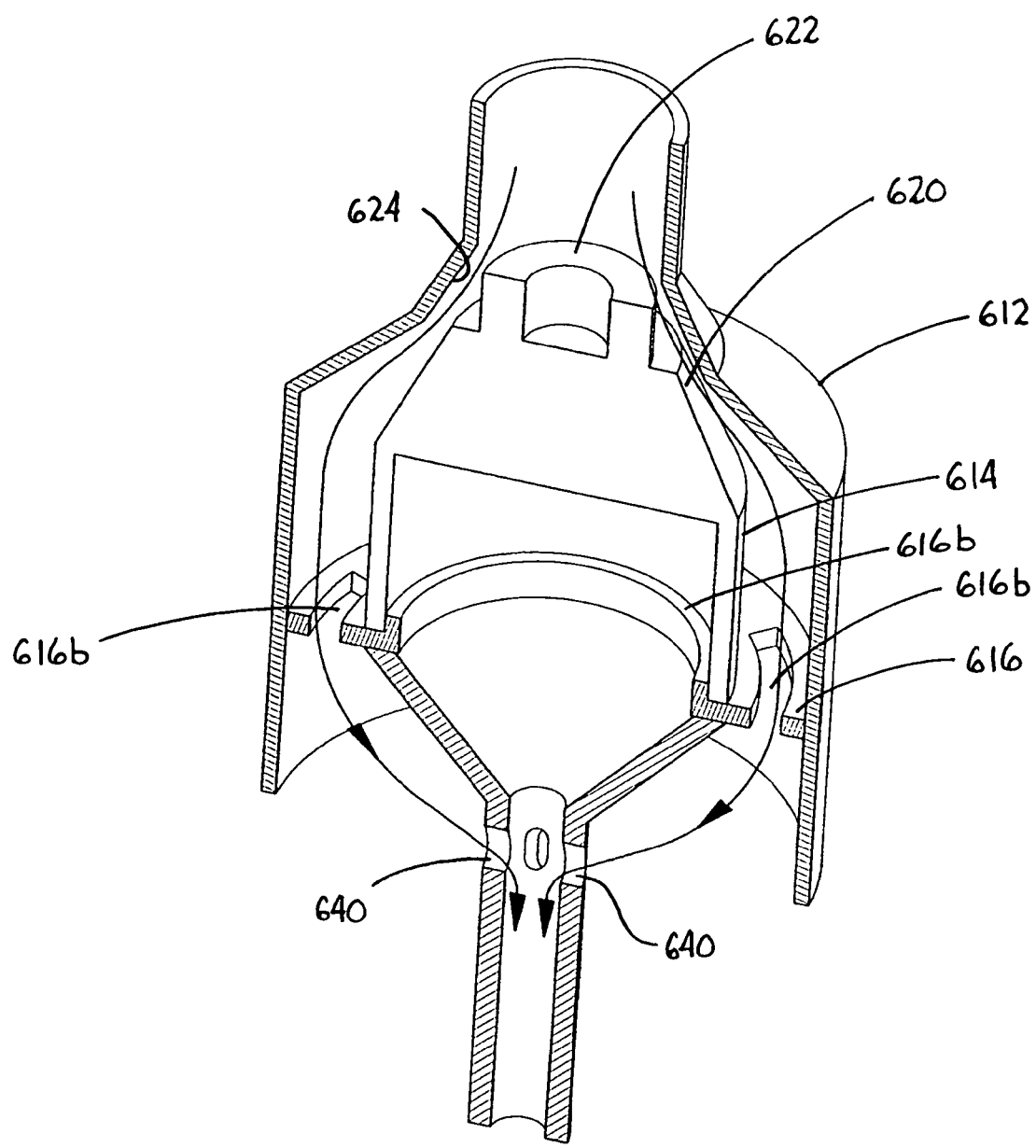
FIG. 25 is a side, cross-sectional, perspective view of the IV catheter shown in FIG. 24

FIGS. 24 and 25 illustrate another embodiment of the presently disclosed IV catheter assembly 610. Catheter assembly 610 includes a proximal housing 612, a seal member 614, a locking ring 616 and a tubular member 618. Proximal housing 612 defines an inlet 602 and a chamber 611 having a proximal portion 611a and a distal portion 611b. Seal member 614 is positioned within housing 612 and includes a sealing portion 620 and raised sections 622. Sealing portion 620 is positioned to engage a seating surface 624 formed on an internal wall of housing 612. Seal member 614, unlike the seal members described above, does not have any windows or channels. Tubular member 618 defines a lumen which is in fluid communication with distal portion 611b of chamber 611.

Locking ring or member 616 defines an annular member which has an outer periphery which is secured to an internal surface of housing 612 and an inner periphery which centrally locates seal member 614 within housing 612. Although not shown, the outer periphery of locking ring can be secured to the inner surface of housing 612 using any known fastening technique. For example, the outer periphery of locking ring 616 may be received in an annular groove (not shown) formed about an inner surface of housing 612. Alternatively, adhesives, pins, etc., may be used to secure locking ring 616 within housing 612. The inner periphery of locking ring 616 is secured to seal member 614. In the embodiment, illustrated, the inner periphery of locking ring 616 includes an annular rim 616a which receive the distal end of seal member 614 to fix seal member 614 to locking ring 616. The distal end of seal member 614 may be secured to rim 616a using, for example, an adhesive. Alternatively, other techniques for securing seal member 614 to locking ring 616 can be used, e.g., adhesives, welding, crimping etc.

As discussed above, seal member 614 does not have any windows or flow channels. However, locking ring 616 includes channels 616b which provided a pathway for fluid to flow about seal member 614. Thus, when sealing portion 620 of seal member 614 is moved away from seating surface 624 of housing 612, fluid will flow from inlet 602 about seal member 614, through channels 616b in locking ring 616 and into openings 640 in tubular member 618. It is envisioned that tubular member 618 can be integrally formed with locking ring 616. Alternatively, tubular member 616 can be held in abutting relation or secured to locking ring 616 using any known technique. As illustrated in FIG. 24, tubular member 618 extends through distal housing 613.

Although embodiments of the disclosure have been described using specific terms, such description is for illustrative purposes only, and it is to be understood that changes and variations may be made without departing from the spirit or scope of the following claims.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:
1. An IV catheter device comprising:
a housing defining a chamber;
a seal member positioned within the chamber, the seal member including a sealing portion which is positioned to engage a seating surface within the housing to seal a proximal portion of the chamber from a distal portion of the chamber; and
a locking member positioned within the chamber of the housing, the locking member being positioned about and engaging the seal member to position the sealing portion of the seal member in engagement with the seating surface, the locking member including at least one channel connecting a proximal portion of the chamber to a distal portion of the chamber;

wherein when the sealing portion of the seal member is moved from engagement with the seating surface within the housing, fluid can flow about the sealing member and through the at least one channel to the distal portion of the chamber.

2. The IV catheter device according to claim 1, wherein the locking member has a substantially annular body.

3. The IV catheter according to claim 2, wherein an external periphery of the locking member is secured to an inner wall of the housing and an internal periphery of the locking member is secured to the seal member.

4. The IV catheter device according to claim 3, wherein the inner periphery of the locking member includes an annular rim configured to receive a distal end of the seal member.

5. An IV catheter device comprising:
a housing defining a chamber;
a seal member positioned within the chamber, the seal member including sealing portion which is positioned to engage a seating surface within the housing to seal a proximal portion of the chamber from a distal portion of the chamber;
a locking member having a substantially annular body positioned within the chamber of the housing, the locking member being positioned about and engaging the seal member to position the sealing portion of the seal member in engagement with the seating surface, the locking member including at least one channel connecting a proximal portion of the chamber to a distal portion of the chamber;
wherein when the sealing portion of the seal member is moved from engagement with the seating surface within the housing, fluid can flow about the sealing member and through the at least one channel to the distal portion of the chamber, wherein the at least one channel includes a plurality of channels positioned about the annular body of the locking member.

6. The IV catheter device according to claim 1, further including a tubular member defining a lumen in fluid communication with the distal portion of the chamber.

7. An IV catheter device comprising:
a housing defining a chamber;
a tubular member extending distally from the housing and defining a lumen, the lumen being in fluid communication with the chamber;
a seal member disposed within the chamber, the seal member having a sealing portion and a septum configured to removably receive an introducer needle, the sealing portion of the seal member being movable into sealing engagement with a portion of the housing; and
a compression member coupled to the seal member, and being configured and dimensioned to apply a compressive force to the septum, the compression member having a substantially cylindrical shape and having an internal surface including at least one friction element, each at least one friction element including an angled, distally extending barb having an apex and a sloped proximal surface, the sloped proximal surface of the barb being configured to facilitate placement of the compression member about the septum and the apex being configured to provide a retention force to retain the compression member about the septum.

8. The IV catheter device according to claim 7, wherein the compression member includes indicia configured to provide an indication that the compression member is properly oriented for placement on the septum.

9. The IV catheter device according to claim 8, wherein the indicia includes one or more cutouts formed on the distal end of the compression member.

10. The IV catheter device according to claim 8, wherein the indicia includes one or more tabs formed on a distal end of the compression member, the one or more tabs further providing an indication that the compression member has been properly positioned on the septum when the distal end of the tabs are positioned flush with a distal face of the septum.

11. An IV catheter device comprising:
a housing defining a chamber;
a tubular member extending distally from the housing and defining a lumen, the lumen being in fluid communication with the chamber;
a seal member disposed within the chamber, the seal member having a sealing portion and a septum configured to removably receive an introducer needle, the sealing portion of the seal member being movable into sealing engagement with a portion of the housing; and
a compression member coupled to the seal member about the septum, the compression member having a substantially cylindrical shape and having an internal surface including at least one friction element, each at least one friction element including an angled, distally extending barb having an apex and a sloped proximal surface, the sloped proximal surface of the barb being configured to facilitate placement of the compression member about the septum and the apex being configured to provide a retention force to retain the compression member about the septum the compression member including indicia configured to provide an indication that the compression member is properly oriented for placement on the septum, the indicia including a plurality of cutouts formed on the distal end of the compression member.

12. An IV catheter device comprising:
a housing defining a chamber;
a tubular member extending distally from the housing and defining a lumen, the lumen being in fluid communication with the chamber;
a seal member disposed within the chamber, the seal member having a sealing portion and a septum configured to removably receive an introducer needle, the sealing portion of the seal member being movable into sealing engagement with a portion of the housing; and
a compression member coupled to the seal member about the septum, the compression member having a substantially cylindrical shape and having an internal surface including at least one friction element, each at least one friction element including an angled, distally extending barb having an apex and a sloped proximal surface, the sloped proximal surface of the barb being configured to facilitate placement of the compression member about the septum and the apex being configured to provide a retention force to retain the compression member about the septum the compression member including indicia configured to provide an indication that the compression member is properly oriented for placement on the septum, the indicia including a plurality of tabs formed on a distal end of the compression member, the one or more tabs further providing an indication that the compression member has been properly positioned on the septum when the distal end of the tabs are positioned flush with a distal face of the septum.

* * * * *